(12) United States Patent
Weber

(10) Patent No.: US 8,969,020 B2
(45) Date of Patent: *Mar. 3, 2015

(54) PEPTIDE SEQUENCE THAT PROMOTES TUMOR INVASION

(75) Inventor: Georg F. Weber, Cincinnati, OH (US)

(73) Assignee: MetaMol Theranostics LLC, Cincinnati, OH (US)

( * ) Notice: Subject to any disclaimer, the term of this patent is extended or adjusted under 35 U.S.C. 154(b) by 512 days.

This patent is subject to a terminal disclaimer.

(21) Appl. No.: 12/854,011

(22) Filed: Aug. 10, 2010

(65) Prior Publication Data

US 2011/0033857 A1    Feb. 10, 2011

Related U.S. Application Data

(63) Continuation of application No. 12/093,340, filed as application No. PCT/US2006/044257 on Nov. 14, 2006, now Pat. No. 7,807,790.

(60) Provisional application No. 60/736,193, filed on Nov. 14, 2005.

(51) Int. Cl.
*G01N 33/574*    (2006.01)

(52) U.S. Cl.
CPC ...... *G01N 33/57484* (2013.01); *G01N 2333/52* (2013.01)
USPC ..................... 435/7.23; 424/130.1

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,223,409 | A | 6/1993 | Ladner et al. |
| 5,225,539 | A | 7/1993 | Winter |
| 2003/0087250 | A1 | 5/2003 | Monahan et al. |
| 2003/0087270 | A1 | 5/2003 | Schlegel et al. |
| 2003/0124128 | A1 | 7/2003 | Lillie et al. |
| 2004/0142865 | A1 | 7/2004 | Weber |

FOREIGN PATENT DOCUMENTS

| | | |
|---|---|---|
| EP | 125023 | 11/1984 |
| EP | 171496 | 2/1986 |
| EP | 173494 | 3/1986 |
| EP | 184187 | 6/1986 |
| EP | 0 259 149 | 3/1988 |
| WO | 86/01533 | 3/1986 |
| WO | 87/02671 | 5/1987 |
| WO | 88/09810 | 12/1988 |
| WO | 89/10134 | 11/1989 |
| WO | 90/02809 | 3/1990 |
| WO | 91/17271 | 11/1991 |
| WO | 92/01047 | 1/1992 |
| WO | 92/09690 | 6/1992 |
| WO | 92/15679 | 9/1992 |
| WO | 92/18619 | 10/1992 |
| WO | 92/20791 | 11/1992 |
| WO | 93/01288 | 1/1993 |

OTHER PUBLICATIONS

EP 11154390.6-2401 Extended European Search Report and European Search Opinion dated Aug. 18, 2011, 7 pages.
He et al. An osteopontin splice variant induces anchorage independence in human breast cancer cells. *Oncogene.* (2006) 25, 2192-2202.
International Search Report issued regarding International Application No. PCT/US2006/044257 (May 16, 2007).
Written Opinion issued regarding International Application No. PCT/US2006/044257 (May 16, 2007).
International Search Report issued regarding International Application No. PCT/US2006/044257 (Sep. 10, 2007).

*Primary Examiner* — Mark Halvorson

(57) ABSTRACT

An isolated sequence SGSSEEKQNAVSSEET (OPNcPEP) SEQ ID NO: 8, and uses thereof. The peptide enhanced soft agar clone formation but did not support the growth of cells in plastic dishes, consistent with supporting anchorage-independence rather than growth. This sequence represented and is unique for a domain around the splice junction of OPN variant -c (OPN-c). OPN-c was expressed in a variety of tumor cell lines, but not in normal tissues (e.g., non-cancerous tissue) or in benign tumors. OPN-c antibody may be administered to a patient with a cancer associated with OPN-c expression to prevent the formation and growth of metastases. OPN-c may be used as a diagnostic to determine whether a patient has a malignant, rather than a benign, growth. OPN-c may be used to detect or identify agents that inhibit or mimic OPN-c expression or activity.

8 Claims, 15 Drawing Sheets

| Gene Category | List Hits | Population Hits | Probability | Benjamini FDR | Bonferroni FDR | Genbank |
|---|---|---|---|---|---|---|
| oxidoreductase activity | 33 | 508 | $5.29 \times 10^{-4}$ | $4.01 \times 10^{-2}$ | $6.01 \times 10^{-1}$ | *AF258341*; AK002110; AK026717; BC014191; *BC015041*; NM_000159; NM_000302; NM_000689; NM_000786; *NM_000903*; NM_001360; NM_001513; NM_002085; NM_002134; *NM_002495*; NM_002631; NM_003142; NM_003273; NM_003366; NM_004551; NM_004718; NM_005002; *NM_005005*; NM_005125; NM_006440; NM_007103; NM_015380; NM_016011; NM_016527; *NM_016593*; NM_017547; *NM_024407*; *NM_025159* |
| cation transporter activity | 15 | 195 | $3.88 \times 10^{-3}$ | $2.20 \times 10^{-1}$ | 1 | AB032996; AB051548; AK002110; NM_001687; NM_001693; *NM_002495*; NM_003366; *NM_003945*; NM_004551; NM_004718; NM_005002; *NM_005005*; NM_005125; NM_007103; *NM_024407* |
| electron transporter activity | 20 | 295 | $4.06 \times 10^{-3}$ | $2.20 \times 10^{-1}$ | 1 | *AF258341*; AK002110; AK056467; NM_000302; NM_000689; *NM_000903*; NM_002085; *NM_002134*; *NM_002495*; NM_002631; NM_004551; NM_004718; NM_005002; *NM_005005*; NM_006440; NM_007103; NM_015959; *NM_016593*; *NM_024407*; NM_030810 |

FIG. 6A

| clone | symbol | avg int | A_V | C_A | C_V | pA_V | pC_A | pC_V |
|---|---|---|---|---|---|---|---|---|
| NM_003839 | TNFRSF11A | 131 | 1.52 | 1.12 | 1.70 | 0.0017 | 0.1013 | 0.0007 |
| NM_021975 | RELA | 194 | 1.79 | 2.03 | 3.64 | 0.0549 | 0.0128 | 0.0032 |
| NM_003998 | NFKB1 | 91 | 1.50 | 1.67 | 2.50 | 0.1609 | 0.0421 | 0.0047 |
| AK057862 | NFKBIB | 1338 | -2.66 | -1.08 | -2.86 | 0.0113 | 0.7413 | 0.0136 |
| NM_006663 | RAI | 155 | -1.82 | -1.24 | -2.25 | 0.0368 | 0.2704 | 0.0145 |
| NM_004556 | NFKBIE | 428 | 1.38 | 1.52 | 2.10 | 0.1822 | 0.0548 | 0.0189 |
| NM_004180 | TANK | 518 | -2.37 | -1.07 | -2.54 | 0.0316 | 0.7384 | 0.0209 |
| NM_020529 | NFKBIA | 8718 | 1.25 | 1.43 | 1.79 | 0.3092 | 0.0784 | 0.0384 |

FIG. 7B

US 8,969,020 B2

PEPTIDE SEQUENCE THAT PROMOTES TUMOR INVASION

RELATED APPLICATIONS

This application is a continuation of co-pending U.S. application Ser. No. 12/093,340 filed May 12, 2008, which claims priority to PCT/US 2006/044257 filed Nov. 14, 2006, which claims priority to U.S. Application Ser. No. 60/736,193 filed Nov. 14, 2005, each of which is expressly incorporated by reference herein in its entirety.

BACKGROUND

The genetic basis of cancer dissemination, also known as metastasis, has been subject to intense debate. Metastasis genes have been identified as stress response genes, which in cancer are deregulated on the levels of aberrant expression and splicing.

Osteopontin is a cytokine that is frequently secreted by cancer cells and plays important roles in their ability to metastasize. Its expression is necessary and may be sufficient for invasiveness by breast tumors. Multiple metastatic breast cancer cell lines express osteopontin, and transfection of the osteopontin gene into benign tumorigenic human breast epithelial cell lines conveys invasive behavior. Increasing the expression of osteopontin, or transfection of osteopontin encoding cDNA into a previously benign cell line, is sufficient to produce a metastatic phenotype in a rat mammary model. High osteopontin levels in the plasma or tumor are an adverse prognostic factor in breast carcinoma.

Osteopontin derived from various cellular sources is heterogeneous and has been described previously, but the underlying biochemical processes of the heterogeneity are incompletely understood. Tumor-derived osteopontin was differentially detected by Western blotting and in a set of sandwich ELISA setups, characterized by using various antibody combinations. Distinctly sized osteopontin forms are secreted by tumor cells and their non-transformed counterparts. Cancer cells may secrete a splice variant that has a deletion in its N-terminal portion, for example, an osteosarcoma secreted a smaller form of osteopontin than the predominant product generated by non-transformed bone cells. Secretion of the smaller osteopontin form correlated with anchorage-independence, which may reflect a loss of adhesion to osteopontin, because in contrast to host osteopontin, tumor-derived osteopontin fails to associate with the extracellular matrix and remains soluble.

In humans, two osteopontin splice variants with deletions of exon 4 (termed osteopontin-c) or exon 5 (termed osteopontin-b) have been described and both variants are expressed in glioma cells. Differences in the physiologic roles between these variants have not been studied. Splice variants of osteopontin may be expressed selectively in malignant tumors and facilitate their dissemination. Functional alterations associated with the alternatively spliced exons may account for the observed differences between host and tumor osteopontin.

BRIEF DESCRIPTION OF THE DRAWINGS

FIGS. 6A and 6B show the alterations in gene expression profiles induced by OPN-c and OPN-a in soft agar.

FIGS. 7A and 7B show changes in NF-κB gene expression induced by OPN-a or OPN-c in soft agar.

DETAILED DESCRIPTION

Figure 1A:
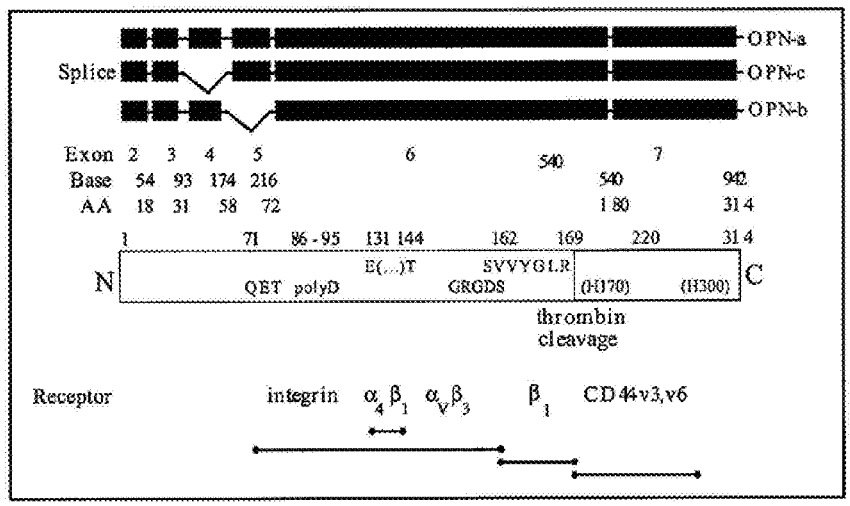
FIG. 1A shows the schematic structure of osteopontin (OPN) and various features of the protein.

Osteopontin (OPN) is a cytokine that is essential for cellular immunity, its full-length form, osteopontin-a (OPN-a), is SEQ ID NO: 1 and its coding sequence is SEQ ID NO: 2. The full-length form of OPN-b is SEQ ID NO: 3 and its coding sequence is SEQ ID NO: 4. The full-length form of OPN-c is SEQ ID NO: 5 and its coding sequence is SEQ ID NO: 6. OPN-b and OPN-c are splice variants of OPN-a and lack exons 5 and 4, respectively, of OPN's six translated exons. Some forms of osteopontin support the invasiveness of cancer cells. Invasiveness is equivalent to the penetration by cancer cells through tissue barriers, the destruction of surrounding tissue, anchorage independent survival of the cancer cells, and/or the colonization of other organs known as metastasis. Metastatic tumor cells are referred to as malignant. This is in contrast to tumor cells that do not invade the surrounding tissue, which are referred to as benign.

OPN-c (SEQ ID NOs: 6 (nucleotide) and 7(protein)) was expressed in a variety of tumor cell lines, but not in normal tissues (e.g., non-cancerous tissue) or in benign tumors. In one embodiment, methods for therapy in a patient having a cancer associated with OPN-c expression are disclosed. In another embodiment, methods for determining whether a patient has a malignant or benign growth are also disclosed. In another embodiment, methods for detecting or identifying agents that inhibit or mimic the expression or activity of OPN-c are disclosed.

Isolated and/or recombinant forms of an OPNc peptide (OPNcPEP), SGSSEEKQNAVSSEET SEQ ID NO: 8, and the corresponding domain of the OPN-c protein (OPN-c polypeptide) SEQ ID NO: 7, are disclosed. The terms peptide and polypeptide are generally used in reference to amino acid polymers that are shorter than proteins. However, unless specifically noted, there is no other intended distinction between peptides, polypeptides, and proteins; as used herein, the peptide encompasses modifications, truncations, etc. of SEQ ID NO: 8

SEQ ID NO: 8 (OPNcPEP) enhanced soft agar clone formation but did not support the growth of cells in plastic dishes, consistent with supporting cell anchorage-independence rather than cell growth. SEQ ID NO: 8 represents and is unique for a domain around the splice junction of OPN variant-c (OPN-c).

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. All publications, patent applications, patents, and other references disclosed herein are incorporated by reference in their entirety.

A "recombinant protein" is a protein produced by recombinant DNA techniques, where generally, DNA encoding OPNcPEP is inserted into a suitable expression vector that is in turn used to transform a host cell to produce the heterologous protein. The phrase "derived from", when used with respect to a recombinant OPN-c gene, includes within the meaning of "recombinant protein" those proteins having an amino acid sequence of a natural occurring OPN-c protein, or a similar amino acid sequence which is generated by mutations including substitutions and deletions (including truncation) of a naturally occurring form of the protein or of the biologically active peptide OPNcPEP. As disclosed are isolated OPN-c polypeptides that are isolated from, or otherwise substantially free from other cellular proteins, especially other factors which may normally be associated with the OPN-c polypeptide. "Substantially free of other cellular proteins", with "other cellular proteins" also referred to herein as "contaminating proteins", or "substantially pure or purified preparations" encompass preparations of OPNcPEP having less than about 20% (dry weight) contaminating protein in one embodiment, and less than about 5% (dry weight) contaminating protein in another embodiment.

Functional forms of the proteins are prepared as purified preparations using a cloned gene as described herein. The term "purified", when referring to a peptide, DNA, or RNA sequence, indicates that the molecule is present in the substantial absence of other biological macromolecules, such as other proteins. In one embodiment, "purified" indicates at least about 80% dry weight of the molecule. In another embodiment, "purified" indicates at least about 95-99% dry weight of the molecule. In another embodiment, "purified" indicates at least about 99.8% dry weight of the molecule. The percentages are given in comparison to biological macromolecules of the same type present; water, buffers, and other small molecules, especially molecules having a molecular weight less than about 5000, can be present. The term "pure" as used herein has the same numerical parameters as "purified" described above. "Isolated" and "purified" are not meant to encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In various embodiments, purified OPN-c polypeptide preparations lack any contaminating proteins from the same cell from which OPN-c is normally produced, as can be accomplished by recombinant expression of, for example, a human OPN-c protein in a non-human cell.

In one embodiment, a OPN-c polypeptide includes the amino acid sequence SGSSEEKQNAVSSEET SEQ ID NO. 8. In one embodiment, OPN-c polypeptides have amino acid sequences evolutionarily related to the above SEQ ID NO. 8. The term "evolutionarily related to", with respect to amino acid sequences of OPN-c polypeptides, refers to both proteins having amino acid sequences that are present naturally, and also to mutational variants of OPN-c polypeptides that are derived, e.g., by combinatorial mutagenesis. In one embodiment, such related OPN-c polypeptides are at least about 75% homologous with SEQ ID NO: 8. In another embodiment, such related OPN-c polypeptides are at least about 80% homologous with SEQ ID NO. 8. In another embodiment, such related OPN-c polypeptides are at least about 85% homologous with SEQ ID NO.: 8. In another embodiment, such related OPN-c polypeptides are at least about 90% homologous with SEQ ID NO.: 8.

In certain embodiments, an OPN-c polypeptide, such as OPNcPEP SEQ ID NO: 8, is altered to provide homologs of one of the OPN-c polypeptides. Such homologs function in some capacity as either an OPN-c agonist (mimetic) or an OPN-c antagonist, to promote or inhibit only a subset of the biological activities of the naturally-occurring form of the protein. Thus, specific biological effects can be elicited by providing a patient with a homolog of limited function, and with fewer side effects relative to treatment with agonists or antagonists that provide all the biological activities of naturally occurring forms of OPN-c polypeptides. Homologs of each of the OPN-c polypeptides are generated by mutagenesis, such as by discrete point mutation(s), or by truncation. For example, mutations can give rise to homologs that retain substantially the same, or merely a subset, of the biological activity of the OPN-c polypeptide from which it was derived. Alternatively, antagonistic forms can be generated which are able to inhibit the function of the naturally occurring form of the protein, such as by competitively binding to an OPN-c binding protein. In addition, agonistic forms of the polypeptide may be generated which are constitutively active. Thus, the disclosed human OPN-c polypeptide and homologs thereof may be either positive or negative regulators of adhesion independence, expression of oxidoreductases, or other biological functions.

OPN-c polypeptides may be chemically modified to create OPN-c derivatives. Chemical modifications include, but are not limited to, forming covalent or aggregate conjugates with other chemical moieties, such as lipids, phosphate, acetyl groups, etc. Covalent derivatives of OPN-c polypeptides are prepared by linking the chemical moieties to functional groups on amino acid side-chains of the polypeptide, or at the N-terminus or C-terminus of the polypeptide. Modifications may enhance therapeutic or prophylactic efficacy, stability (e.g., ex vivo shelf life, resistance to proteolytic degradation in vivo), or may be post-translational modifications. An example of post-translational modifications includes alterations of the phosphorylation pattern of the protein caused by kinases and phosphatases, e.g., the serines in the OPNcPEP SEQ ID NO: 8 are substrates for Golgi Kinase. Such modified polypeptides, when designed to retain at least one activity of the naturally occurring form of the polypeptide, or to produce specific antagonists thereof, are included as functional equivalents of the disclosed OPN-c polypeptides. Such modified polypeptides can be produced, for example, by amino acid substitution, deletion, and/or addition.

Whether a change in the amino acid sequence of a peptide results in a functional OPN-c homolog (i.e., the resulting protein mimics or antagonizes the wild-type form) can be readily determined. For example, one can assess the ability of the variant peptide to produce a response in cells in a fashion similar to the wild-type polypeptide, or to competitively inhibit such a response. Polypeptides in which more than one replacement has taken place can readily be similarly evaluated.

In one embodiment, isolated nucleic acid molecules that encode the OPN-c polypeptide SEQ ID NO: 8 are disclosed. In one embodiment, nucleic acids that encode the sequence of OPNcPEP SEQ ID NO: 8, or biologically active portions thereof, are disclosed. As used herein, the term "nucleic acid molecule" is includes DNA molecules (e.g., cDNA or genomic DNA) and RNA molecules (e.g., mRNA). The nucleic acid molecule may be single-stranded or double-stranded. In one embodiment, it is double stranded. An "isolated" nucleic acid molecule is free of sequences that naturally flank the nucleic acid (i.e., sequences located at the 5' and 3' ends of the nucleic acid) in the genomic DNA of the organism from which the nucleic acid is derived. For example, in embodiments, the isolated OPN-c nucleic acid molecule may contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, may be free of other cellular material. In one embodiment, the disclosed isolated OPN-c nucleic acid molecule is naturally occurring. In one embodiment, the disclosed isolated OPN-c nucleic acid molecule comprises the nucleotide sequence SEQ ID NO: 36. This cDNA comprises sequences encoding OPNcPEP SEQ ID NO: 8. In one embodiment, a nucleic acid molecule contains all or a portion of the sequence encoding SGSSEEKQNAVSSEET SEQ ID NO: 8. In one embodiment, a nucleic acid molecule contains a sequence at least about 85% homologous to SEQ ID NO: 36. In one embodiment, a nucleic acid molecule contains a sequence at least about 90% homologous to SEQ ID NO: 36. In one embodiment, a nucleic acid molecule contains a sequence at least about 95% homologous to SEQ ID NO: 36.

The disclosed nucleic acid molecule may comprise only a portion of the coding region for SGSSEEKQNAVSSEET SEQ ID NO: 8, e.g., a fragment encoding a biologically active portion of SEQ ID NO: 8. The ability of a portion of OPNcPEP SEQ ID NO: 8 to modulate biological function can be determined in a number of assays known to one skilled in the art, e.g., by measuring the ability of a portion of OPNcPEP SEQ ID NO: 8 to enhance soft agar clone formation or to induce the gene expression of oxidoreductases (e.g. GPX-4). Nucleic acid fragments encoding biologically active portions of OPNcPEP can be prepared by isolating a portion of SEQ ID NO: 36, expressing the encoded protein or peptide (e.g., by recombinant expression in vitro) and assessing the biological function.

In one embodiment, nucleic acid molecules encoding SEQ ID NO: 8 are naturally-occurring nucleic acid molecules. As used herein, a "naturally-occurring" nucleic acid molecule is an RNA or DNA molecule having a nucleotide sequence that occurs in nature (e.g., encodes a natural protein). Such nucleic acid molecules encoding OPN-c polypeptides from other species, and thus which have a nucleotide sequence which differs from the human sequence, are included. In one embodiment, the disclosed OPN-c nucleic acid molecule is isolated from a vertebrate organism. In one embodiment, the disclosed OPN-c nucleic acid molecule is mammalian. In one embodiment, the disclosed OPN-c nucleic acid molecule is human. In addition to the OPN-c nucleotide sequence, one skilled in the art will appreciate that DNA sequence polymorphisms that lead to changes in the amino acid sequences of OPN-c may exist within a population (e.g., the human population). Such genetic polymorphism in the OPN gene may exist among individuals within a population due to natural allelic variation. Any and all such nucleotide variations and resulting amino acid polymorphisms in OPN-c that are the result of natural allelic variation and that do not alter the functional activity of OPN-c are included. Nucleic acid molecules corresponding to natural allelic variants and homologues of the disclosed OPN-c cDNAs can be isolated based on their homology to the OPN-c nucleic acid disclosed herein using the human cDNA, or a portion thereof, as a hybridization probe according to standard hybridization techniques under stringent hybridization conditions. As used herein, "hybridizes under stringent conditions" includes conditions for hybridization and washing under which nucleotide sequences at least 60% homologous to each other typically remain hybridized to each other. In one embodiment, the conditions are such that at least sequences at least 65% homologous to each other typically remain hybridized to each other. In one embodiment, the conditions are such that at least 70% homologous to each other typically remain hybridized to each other. In one embodiment, the conditions are such that at least 75% homologous to each other typically remain hybridized to each other. Such stringent conditions are known to one skilled in the art and are also readily determined, e.g., Current Protocols in Molecular Biology, John Wiley & Sons, N.Y. (1989), 6.3.1-6.3.6.

Besides naturally occurring allelic variants of the OPN-c sequence that may exist in the population, one skilled in the art will further appreciate that changes may be introduced by mutation into the nucleotide sequence SEQ ID NO: 36, thereby leading to changes in the amino acid sequence of the encoded SEQ ID NO: 8 or the corresponding sequence within SEQ ID NO: 7, without altering the functional ability of the OPN-c peptide. For example, nucleotide substitutions leading to amino acid substitutions at non-essential amino acid residues may be made in the sequence. A "non-essential" amino acid residue is one that can be altered from the wild-type sequence of SEQ ID NO: 8 without altering the biological activity thereof, whereas an "essential" amino acid residue is required for this activity.

In one embodiment, an OPN-c nucleic acid molecule encodes a protein which comprises a sequence at least about 75% homologous to SGSSEEKQNAVSSEET SEQ ID NO: 8. In one embodiment, an OPN-c nucleic acid molecule encodes a protein which comprises a sequence at least about 81.3% homologous to SEQ ID NO: 8. In one embodiment, an OPN-c nucleic acid molecule encodes a protein which comprises a sequence at least about 87.5% homologous to SEQ ID NO: 8. In one embodiment, an OPN-c nucleic acid molecule encodes a protein which comprises a sequence at least about 93.7% homologous to SEQ ID NO: 8. In one embodiment, an OPN-c nucleic acid molecule encodes a protein which comprises a sequence at least about 95% homologous to SEQ ID NO: 8. In one embodiment, an OPN-c nucleic acid molecule encodes a protein which comprises SEQ ID NO: 8.

In one embodiment, SEQ ID NO: 8 is truncated to generate mimetics, e.g. peptide or non-peptide agents, which are able to disrupt, with binding proteins or with interactors (i.e., other molecules that may bind, such as small molecules), a disclosed human OPN-c protein. This may include, but is not limited to the elimination of a variable number of amino acids from the N-terminal and the C-terminal end of the peptide, such as SSEEKQNAVSS (SEQ ID NO: 38), EEKQNAV (SEQ ID NO: 35), or EKQNA (SEQ ID NO: 39). Thus, previously described mutagenic techniques are also useful to map the determinants of the OPN-c polypeptides which participate in protein-protein interactions. Such interactions can be involved in, e.g., binding of the disclosed human OPN-c polypeptide to proteins that may function upstream (including both activators and repressors of its activity) or downstream of the OPN-c polypeptide (SEQ ID NO: 8), whether they are positively or negatively regulated by it. To illustrate, the critical residues of a OPN-c polypeptide SEQ ID NO: 8 that are involved in molecular recognition of interactor proteins upstream or downstream of an OPN-c can be determined and used to generate OPN-c-derived peptidomimetics which competitively inhibit binding of the naturally occurring OPN-c polypeptide SEQ ID NO: 8 to that moiety. By employing, e.g., scanning mutagenesis to map the amino acid residues of OPNcPEP involved in binding other extracellular proteins, peptidomimetic modulating agents can be generated that mimic those residues of the OPN-c polypeptide that facilitate the interaction. Such mimetics may then be used to interfere with the normal function of a OPN-c polypeptide. For example, non-hydrolyzable peptide analogs of such residues can be generated using benzodiazepine (e.g., Freidinger et al., Peptides: Chemistry and Biology, G. R. Marshall Ed., ESCOM Publisher: Leiden, Netherlands 1988), azepine (e.g., Huffman et al., Peptides: Chemistry and Biology, G. R. Marshall Ed., ESCOM Publisher: Leiden, Netherlands, 1988), substituted gamma-lactam rings (Garvey et al., Peptides: Chemistry and Biology, G. R. Marshall Ed., ESCOM Publisher: Leiden, Netherlands, 1988), keto-methylene pseudopeptides (Ewenson et al. (1986) J Med Chem 29:295; Ewenson et al., Peptides: Structure and Function (Proceedings of the 9$^{th}$ American Peptide Symposium) Pierce Chemical Co. Rockford Ill. 1985), β-turn dipeptide cores (Nagai et al. (1985) Tetrahedron Lett 26:647; Sato et al. (1986) J Chem Soc Perkin Trans 1:1231), and β-aminoalcohols (Gordon et al. (1985) Biochem Biophys Res Commun 126:419; Dann et al. (1986) Biochem Biophys Res Commun 134:71).

In another embodiment, the coding sequences for the polypeptide can be incorporated as a part of a fusion gene including a nucleotide sequence encoding a different protein to generate a fusion protein or chimeric protein. A "chimeric protein" or "fusion protein" is a fusion of a first amino acid sequence encoding OPNcPEP with a second amino acid sequence defining a domain (e.g. protein portion) foreign to and not substantially homologous with any domain of one of the mammalian OPN-c polypeptides. A chimeric protein may present a foreign domain, which is found (albeit in a different protein) in an organism that also expresses the first protein, or it may be an "interspecies", "intergenic", etc. fusion of protein structures expressed by different kinds of organisms. In general, a fusion protein can be represented by the general formula X-OPNcPEP-Y, wherein OPNcPEP represents a portion of the peptide derived from one of the human OPN-c polypeptides, and X and Y are independently absent or represent amino acid sequences which are not related to one of the human OPN-c sequences in an organism, including naturally occurring mutants. Fusion proteins can also facilitate the expression of proteins, and accordingly can be used to express the disclosed OPNcPEP. For example, OPN-c polypeptides can be generated as glutathione-S-transferase (GST-fusion) proteins. Such GST-fusion proteins can enable easy purification of the OPN-c polypeptide, e.g., by the use of glutathione-derivitized matrices (e.g., Current Protocols in Molecular Biology, Eds. Ausubel et al. (N.Y., John Wiley & Sons, 1991). In another embodiment, a fusion gene coding for a purification leader sequence, such as a poly-(His)/enterokinase cleavage site sequence at the N-terminus of the desired portion of the recombinant protein, allows purification of the expressed fusion protein by affinity chromatography using a Ni$^{2+}$ metal resin. The purification leader sequence can then be subsequently removed by enterokinase treatment to provide the purified protein (e.g., Hochuli et al. (1987) J. Chromatography 411:177; Janknecht et al. PNAS 88:8972, 1991). Techniques for making fusion genes are known to one skilled in the art. Essentially, joining of various DNA fragments coding for different polypeptide sequences is performed in accordance with conventional techniques, employing blunt-ended or stagger-ended termini for ligation, restriction enzyme digestion to provide appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed to generate a chimeric gene sequence (e.g., Current Protocols in Molecular Biology, eds. Ausubel et al. John Wiley & Sons: 1992).

In one embodiment, the disclosed fusion proteins contain a detectable label or a matrix-binding domain. Fusion protein preparation is often desirable when producing an immunogenic fragment of an OPN-c polypeptide. For example, the VP6 capsid protein of rotavirus can be used as an immunologic carrier protein for portions of the OPN-c polypeptide, either in the monomeric form or in the form of a viral particle. The nucleic acid sequences corresponding to the portion of a subject OPN-c polypeptide to which antibodies are to be raised can be incorporated into a fusion gene construct which includes coding sequences for a late vaccinia virus structural protein to produce a set of recombinant viruses expressing fusion proteins comprising OPN-c epitopes as part of the virion. It has been demonstrated, with immunogenic fusion proteins utilizing the Hepatitis B surface antigen, that recombinant Hepatitis B virions can be utilized. Similarly, chimeric constructs coding for fusion proteins containing a portion of an OPN-c polypeptide and the poliovirus capsid protein can be created to enhance immunogenicity of the set of polypeptide antigens (e.g., EP Publication No: 0259149; Evans et al. (1989) Nature 339:385; Huang et al. (1988) J. Virol. 62:3855; Schlienger et al. (1992) J. Virol. 66:2).

In one embodiment, a compound that inhibits the activity of SEQ ID NO: 8 is administered. Unless specifically noted, the term "compound" may be used herein interchangeably with "test compound", "agent", "candidate therapeutic agent", etc. The compound may be at least one peptide and/or non-peptide administered to ameliorate the condition of a patient with an OPN-c expressing cancer. Non-peptide compounds include, but are not limited to, chemical compounds (e.g., small molecules) and antibodies. Compounds that inhibit OPN-c polypeptide activity can be administered to patients with OPN-c expressing cancers or to reduce the likelihood that a patient will develop such a cancer, as either an initial or recurring event. In one embodiment, compounds specifically inhibit OPN-c (e.g., OPN-c polypeptides), but absolute specificity is not necessarily required. An agent specifically inhibits OPN-c when it inhibits OPN-c to a greater extent than it inhibits OPN-a or OPN-b, or when the agent inhibits OPN-c but does not inhibit OPN-a or OPN-b to any detectable extent. As with compounds that inhibit the expression of OPN-c mRNA, compounds that specifically bind (or otherwise inhibit the activity of) OPN-c polypeptides can be administered to patients at risk of developing an OPN-c expressing cancer (e.g., healthy patients with a family history of cancer, patients who have been treated (e.g., by surgery, with chemotherapies, or with radiation therapies) for an OPN-c expressing cancer that may recur, etc.). Physicians, in consult with each other and their patients, can determine whether a given patient's risk (whether imposed by family history or personal history (e.g., expression of particular molecular markers such as BRCA-1, BRCA-2, or PSA, or certain events or circumstances, such as heavy smoking or exposure to carcinogens such as asbestos or radiation, including nuclear or light (e.g., ultraviolet) energy)) is sufficient to merit treatment with the disclosed agent. Any of these compounds can be combined with any known method of cancer treatment or prevention. For example, an anti-OPN-c can be administered in connection with (i.e., before, during or after) a surgical procedure in which an OPN-c-associated tumor is physically removed from a patient. Similarly, an anti-OPN-c can be administered in connection with (i.e., before, during or after) a radiation treatment or a course of chemotherapy.

Various antibodies have been synthesized that recognize distinct epitopes of OPN. One antibody targets exon 4, and thus fails to recognize OPN-c (Rittling et al., Biochem. Biophys. Res. Commun. 250:287 (1998); Kon et al., J. Cell Biochem. 77:487 (2000)). Polyclonal antibodies generated against OPN and isolated from human milk inhibited the growth stimulatory effect of OPN in human prostate carcinoma cancer cells (Thalmann et al., Clin. Cancer Res. 5:2271 (1999)). These did not target OPN-c specifically, but instead inhibited all forms of OPN. Anti-OPN-c antibodies administered to human patients can be "humanized" by methods known in the art. The antibodies administered can be monoclonal antibodies. Synthetic peptides are polymers of amino acid residues that can be chemically synthesized or produced by recombinant techniques (the amino acids are linked together by amide bonds formed between the carboxyl group of one amino acid and the amino group of another).

Small molecules are chemical compounds that affect the phenotype of a cell or organism by, e.g., modulating the activity of a specific protein or nucleic acid within a cell. As with other anti-OPN-c compounds, small molecules may affect a cell by directly interacting with OPN-c or by interacting with a molecule that acts upstream or downstream of the biochemical cascade that results in decreased OPN-c expression or activity.

In one embodiment, a method for generating sets of combinatorial and truncation mutants of OPNcPEP is disclosed. Such methods are useful to identify potential variant sequences (e.g. homologs) that modulate an OPN-c bioactivity. Screening such combinatorial libraries generates, e.g., novel OPN-c homologs, that can act as either agonists or antagonists or, alternatively, possess novel activities. To illustrate, combinatorially derived homologs can be generated to have increased potency relative to a naturally occurring form. Likewise, OPN-c homologs can be generated by a combinatorial approach to selectively inhibit (antagonize) naturally occurring OPN-c. Moreover, manipulation of certain domains of OPN-c can provide domains more suitable for use in fusion proteins.

Inhibiting OPN-c expression and/or activity may reduce or prevent cancer and or its effects. To inhibit OPN-c expression, one can administer one or more inhibitory agents, such as an antisense RNA sequence, a small inhibitory RNA (siRNA), or a ribozyme, any of which can be designed to target a sequence within OPN-c, e.g., a sequence exclusively within this splice form. For example, the exon 3/exon 5 junction is a target of OPN-c-specific therapies. The disclosed methods are not limited to agents that inhibit OPN-c by any particular mechanism.

OPN-c activity is inhibited by inhibited translation of the respective mRNAs. This can be accomplished using small RNA endonucleases, called ribozymes, that cleave the phosphodiester bond of substrate RNA, thus specifically inhibiting the expression of target genes. Ribozymes are structured RNAs that catalyze chemical reactions resulting in specific breakdown of OPN-c RNAs. Trans-acting hammerhead ribozymes contain a catalytic domain and flanking regions, which allow hybridization to the target sequence. Short stretches of RNA (possibly as low as 19 nucleotides) may suffice to generate catalytic activity. OPN mRNA was shown to be amenable to targeting by ribozymes, where three hammerhead ribozymes designed to cleave three different regions of OPN mRNA reduced OPN expression in a subset of transformed cells. These cells were less tumorigenic and metastatic (Feng et al., Clin. Exp. Metast. 13:453 (1995). These ribozymes cleaved within the C-terminal half of the OPN mRNA, thereby targeting all three OPN splice forms (OPN-a, OPN-b and OPN-c). In contrast, the present method discloses ribozymes that specifically inhibit expression of OPN-c mRNA, but not of the other splice variants (OPN-a and OPN-b) mRNA. For example, a mRNA sequence including the exon 3/exon 5 splice junction and flanking sequences can be used to select a catalytic RNA having a specific ribonuclease activity specific for OPN-c (e.g., Bartel and Szostak, Science 261:1411 (1993); Krol et al., Bio-Techniques 6:958-976 (1988)).

Generally, "antisense" RNA sequences are complementary to all or a part of the coding sequence of an mRNA, although there may be some "mismatch" so long as the antisense RNA hybridizes with and inhibits translation of the mRNA. Providing antisense oligonucleotides to a patient intends to prevent translation of proteins associated with a particular disease state. OPN antisense molecules have been expressed by stably transfecting cells with a mammalian expression vector containing an OPN cDNA fragment in an inverted orientation. The antisense RNA was capable of targeting all forms of OPN mRNA. The disclosed methods targets OPN-c mRNA specifically. An antisense RNA that targets the exon 3/exon 5 splice junction will only inhibit translation of OPN-c mRNA; other OPN forms continue to be translated. In one embodiment, the antisense oligonucleotide is an RNA molecule (e.g., 18-mer, 19-mer, 20-mer, 21-mer, or 30-mer), complementary to the region including and flanking the splice junction of OPN-c (e.g., nucleotides 84-103, corresponding to OPN-c mRNA).

Antisense nucleic acids are administered to a patient according to protocols known in the art. In one embodiment, they are injected into a particular tissue or generated in situ and, in either event, will hybridize with or specifically bind to the OPN-c mRNA splice variant, thereby inhibiting expression of the encoded protein. In another embodiment, antisense nucleic acids are administered systemically and may be modified to target selected cells. For example, antisense nucleic acids can be linked to antibodies or other proteins (e.g., receptor ligands) that specifically bind to cell surface receptors or other components associated with the target cell type. Similarly, nucleic acids can include agents that facilitate their transport across the cell membrane (e.g., Letsinger et al., Proc. Natl. Acad. Sci. USA 86:6553 (1989); Lemaitre et al., Proc. Natl. Acad. Sci. USA 84:648 (1987); WO 88/09810) or the blood-brain barrier (e.g., WO 89/10134). Nucleic acids can be modified with intercalating agents as disclosed in Zon, Pharm. Res. 5:539 (1988). To achieve sufficient intracellular concentrations of antisense nucleic acids, one can express them in vectors having a strong promoter (e.g., a strong pol II or pol III promoter). In other embodiments, antisense nucleic acids can be α-anomeric nucleic acids, which form specific double-stranded hybrids with complementary RNA in which, contrary to the usual β-units, the strands run parallel to each other (Gaultier et al., Nucleic Acids Res. 15:6625 (1987)). Antisense nucleic acids can comprise a 2'-o-methylribonucleotide (Inoue et al., Nucleic Acids Res. 15:6131 (1987) or a chimeric RNA-DNA analog (Inoue et al., FEBS Lett. 215: 327 (1987)).

Small inhibitory RNAs (siRNAs) are generally short (e.g., 21-23 nucleotides) double stranded RNA (dsRNA) containing 1-2 nucleotide 3' overhangs. Because one strand of the dsRNA is homologous to OPN-c mRNA, siRNA is expected to direct OPN-c RNA cleavage by the RNAseIII-like enzyme Dicer within the RNA induced silencing complex (RISC). siRNA targeting of OPN-c mRNAs is achieved by introducing a double-stranded RNA homologous to the sequence to be cleaved (e.g., the exon 3/exon 5 splice junction of OPN-c) (Tuschl et al., Genes Dev. 13:3191 (1999)). Delivery methods are the same as or similar to those used for antisense molecules.

Nucleic acid modifications can be introduced to increase nucleic acid intracellular stability and half-life. Modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. Modified bases are known to one skilled in the art.

Providing RNA-based agents, such as those described above, can at least partially silence OPN-c mRNA; e.g., mRNAs of this splice form can be degraded, inhibited, or otherwise rendered inactive to an extent that they fail to substantially contribute to pathogenesis (e.g., cancer, tumor growth, or metastases) and there is improvement by an objective sign or clinical symptom, or there is a decreased risk that an OPN-c expressing cancer will occur, grow, spread, or recur. Dosages, formulations, and routes of administering OPN-c inhibitors may vary and are known in the art. Nucleic acid may be incorporated into a recombinant vector and introduced into a cell, tissue, or whole animal by various methods such as liposome-mediated, receptor-mediated, conjugation with metal particles and used with a particle gun, and association with positively charged polymers. The dosages vary with the process and route of application used. For adenoviral applications, dosages may range from a single dose to daily infusions for 5 days every 3 weeks at about $3 \times 10^8$ to about $3 \times 10^{12}$ viral particles. Other doses, intervals, etc. are known to one skilled in the art. The amount of any agent that inhibits OPN-c, whether that agent inhibits the expression or activity of this splice form, is a "therapeutically effective" amount (e.g., an amount sufficient to improve an objective sign or clinical symptom, or a decreased risk that an OPN-c expressing cancer will occur, grow, spread, or recur).

One embodiment discloses methods to screen for modulating agents, including OPN-c homologs, that are either agonists or antagonists of the normal cellular function of SEQ ID NO: 8. Another embodiment discloses methods to screen for agents that specifically inhibit the expression of SEQ ID NO: 8 by either the transcription of DNA into mRNA and/or the translation of mRNA into protein, or the activity of OPNcPEP. Any class of compounds, including those available in cDNA, synthetic, or chemical libraries can be used in the method. Alternatively, the agent may be a natural extract (e.g., a plant extract) or homogenate, or isolated therefrom. Such compounds include, but are not limited to, antisense oligonucleotides, ribozymes, siRNAs, small molecules, antibodies, biologicals, and/or peptides. Such compounds can be collected or assembled into libraries for high throughput screening.

Assays are used to screen for modulating agents, including SEQ ID NO: 8 homologs, which are either agonists or antagonists of the normal cellular function of SEQ ID NO: 8. For example, an indicator composition such as a cell or cell extract is provided which has an OPN-c polypeptide having OPN-c activity. By providing a cell or cell extract system that contains an active OPN-c, effects on OPN-c activity brought about by test compounds are indicated. The indicator composition is contacted with a test compound. The effect of the test compound on OPN-c activity, as measured by a change in the indicator composition, is determined to thereby identify a compound that modulates the activity of an OPN-c polypeptide. A statistically significant change, either decrease or increase, in OPN-c activity in the presence of the test compound, relative to what is detected in the absence of the test compound, indicates the test compound as an OPN-c modulating agent. In one embodiment, OPN-c activity is assessed as described in Example 4.

Cell-based assays are used to identify compounds that specifically inhibit the activity of SEQ ID NO: 8 and include cell-based assays of OPN-c expression and/or activity. Candidate compounds are evaluated in assays that reveal the level of OPN-c mRNA or polypeptide expression. For example, a cell expressing OPN-c (healthy or cancerous) is exposed to one or more candidate compounds. Suitable cells include MDA-MB-435 or MDA-MB-231. Exposure may be in vivo or ex vivo, e.g., in cell culture. The level of OPN-c mRNA and/or polypeptide expression in the cell is determined. mRNA expression can be evaluated by Northern blot analysis, RNAse protection assays, a PCR-based amplification assay (e.g., RT-PCR), etc. Polypeptide expression can be evaluated by Western blot analysis or other antibody-based detection assay. Appropriate controls are used, e.g., OPN-c expression and/or activity can be measured in the absence of a compound or in the presence of a compound that has been rendered inactive (e.g., by heat). A compound that decreases the level of OPN-c mRNA or polypeptide expression is an anti-OPN-c compound and may be administered as a therapeutic. Methods also include culturing cells, for example mammalian cells that express an engineered OPN-c cassette. A cassette is a genetic construct, such as a vector, that is used to confer a nucleotide sequence on a cell. In this case the nucleotide sequence belongs to the OPN-c gene. Cells that naturally express OPN-c may also be transfected with an OPN-c expression vector. In either case, cells are exposed to at least one test compound, and OPN-c expression and/or activity is analyzed. Expression can be detected by, e.g., RT-PCR, Northern, and/or Western blot analysis. Activity can be examined by analyzing any OPN-c based event (e.g., inhibition of cellular soft agar clone formation and/or expression of GPX-4). Cassettes that express OPN-c for the purpose of identifying compounds may be stably transformed into cells or expressed from a constitutive or inducible promoter in a plasmid. Cassettes can include at least exons 3 and 5, and all or fragments of the intervening intron. For high throughput screening, the cassette may include a reporter gene, such as luciferase or GFP that functions as an indicator or marker.

These assays, whether performed in vivo or in cell culture, can also be carried out with cells that have been engineered to express or over-express OPN-c (i.e., the expression level may be a natural or a heightened level of expression, which may provide a more sensitive assay condition). For example, cells can be made to express a construct that encodes only an OPN-c transcript, or a biologically active fragment or other mutant thereof, and a heterologous sequence that can be detected. The construct can include a reporter or marker gene (i.e., any gene whose expression may be assayed such as luciferase, a green fluorescent protein (GFP or EGFP), a-glucuronidase (GUS), chloramphenicol transacetylase (CAT), or LacZ, which encodes β-galactosidase. Whether or not a reporter or marker gene is included, OPN-c expression is examined in the presence and absence of a compound; a compound that decreases expression or activity of OPN-c can be tested further in vivo or in vitro for an effect on cellular proliferation, anchorage-independence, or another indication of malignancy. The compound can interact with OPN-c mRNA or polypeptide directly (e.g., by binding to the mRNA or protein) or indirectly (e.g., by binding to a cellular target that regulates OPN-c mRNA or polypeptide expression, such as a transcription factor).

Cell-free assays may be used. High throughput assays maximize the number of compounds surveyed in a given period of time. Assays performed in cell-free systems, such as derived with purified or semi-purified proteins, are referred as "primary" screens in that they can be generated to permit rapid development and relatively easy detection of an alteration in a molecular target which is mediated by a test compound. The effects of cellular toxicity and/or bioavailability of the compound can be generally ignored in the in vitro system, the assay instead being focused primarily on the effect of the compound on the molecular target as may be manifest in an alteration of binding affinity with upstream or downstream elements. In one embodiment, a modulating compound of interest is contacted with interactor proteins which may function upstream (including both activators and repressors of its activity) or downstream of the OPN-c peptide, whether they are positively or negatively regulated by it. To the mixture of the modulating compound and the upstream or downstream element, a composition containing an OPN-c peptide is added. Detection and quantitation of the interaction of OPN-c with its upstream or downstream elements determine a modulating compound's efficacy at inhibiting or potentiating complex formation between OPN-c and the OPN-c-binding elements. The term "interact" as used herein includes detectable interactions between molecules, as can be detected using, e.g., a yeast two hybrid assay. The term interact also includes "binding" interactions between molecules. Interactions may be protein-protein or protein-nucleic acid. Interactions may be between the OPN-c polypeptide and other biomolecules. Efficacy of the modulating compound can be assessed by generating dose response curves from data obtained using various concentrations of the modulating compound. A control assay can be performed to provide a baseline for comparison. In the control assay, isolated and purified OPN-c polypeptide is added to a composition containing the OPN-c-binding element, and complex formation is quantified in the absence of the modulating compound. Complex formation between the OPN-c peptide and an OPN-c binding element may be detected by a variety of techniques. Modulation of complex formation can be quantified using, e.g., detectably labeled proteins such as radiolabeled, fluorescently labeled, or enzymatically labeled OPN-c peptides, by immunoassay, by chromatographic detection, etc.

In one embodiment, methods to determine whether cells in a tumor or any suspicious growth are malignant or benign are disclosed. The methods can be carried out by, for example, obtaining a sample of the tumor or growth and determining whether cells within the sample express OPN-c using any technique known by one skilled in the art, including RT-PCR, Northern, and Western blot analyses. The detection of OPN-c peptides or their encoding sequences indicates a malignant tumor or growth. An absence of OPN-c does not necessarily indicate a non-malignant tumor.

One embodiment discloses antibodies specifically reactive with Ac-SGSSEEKQNAVSSEETC SEQ ID NO: 41. For example, using immunogens derived from SEQ ID NO: 8, e.g. based on the cDNA sequences, anti-peptide antisera or monoclonal antibodies are made by standard protocols (e.g., Antibodies: A Laboratory Manual, Harlow and Lane Eds. (Cold Spring Harbor Press (1988). A mammal, such as mouse, hamster, or rabbit, is immunized with an immunogenic form of SEQ ID NO: 8 (e.g., an antigenic fragment capable of eliciting an antibody response, or a fusion protein as described above). Techniques for conferring immunogenicity on a protein or peptide include conjugation to carriers or other techniques known by one skilled in the art. An immunogenic portion of SEQ ID NO: 8 is administered in the presence of adjuvant. An adjuvant enhances the immune response. The adjuvant most commonly used for antibody generation is Freund's Complete Adjuvant (FCA). Immunization progress can be monitored by antibody titers in plasma or serum. Standard ELISA or other immunoassays can be used with the immunogen as antigen to assess antibody levels. In one embodiment, antibodies are immunospecific for antigenic determinants of SEQ ID NO: 8. Following immunization of an animal with an antigenic preparation SEQ ID NO: 8, anti-OPN-c antisera is obtained and, if desired, polyclonal anti-OPN-c antibodies are isolated from the serum. To produce monoclonal antibodies, antibody-producing cells (lymphocytes) are harvested from an immunized animal and fused by standard somatic cell fusion procedures with immortalizing cells such as myeloma cells to yield hybridoma cells (e.g., hybridoma technique of Koehler and Milstein (1975) Nature, 256: 495), the human B-cell hybridoma technique (Kozbar et al., (1983) Immunology Today, 4: 72), the EBV-hybridoma technique to produce human monoclonal antibodies (Cole et al., (1985) Monoclonal Antibodies and Cancer Therapy, Alan R. Liss, Inc. pp. 77-96). Hybridoma cells are screened immunochemically for the production of antibodies specifically reactive with SEQ ID NO: 8 and monoclonal antibodies are isolated from a culture comprising such hybridoma cells.

As an alternative to preparing monoclonal antibody-secreting hybridomas, a monoclonal anti-OPN-c antibody is identified and isolated by screening a recombinant combinatorial immunoglobulin library (e.g., an antibody phage display library) with SEQ ID NO: 8 to thereby isolate immunoglobulin library members that bind OPN-c. Kits for generating and screening phage display libraries are commercially available (e.g., Pharmacia Recombinant Phage Antibody System, Catalog No. 27-9400-01; Stratagene SurfZAP™ Phage Display Kit, Catalog No. 240612). Examples of methods and reagents amenable to generate and screen antibody display library are found in, e.g., Ladner et al. U.S. Pat. No. 5,223, 409; Kang et al. WO 92/18619; Dower et al. WO 91/17271; Winter et al. WO 92/20791; Markland et al. WO 92/15679; Breitling et al. WO 93/01288; McCafferty et al. WO 92/01047; Garrard et al. WO 92/09690; Ladner et al. WO 90/02809; Fuchs et al. (1991) Bio/Technology 9:1370; Hay et al. (1992) Hum Antibod Hybridomas 3:81; Huse et al. (1989) Science 246:1275; Griffiths et al. (1993) EMBO J 12:725; Hawkins et al. (1992) J Mol Biol 226:889; Clarkson et al. (1991) Nature 352:624; Gram et al. (1992) PNAS 89:3576; Garrad et al. (1991) Bio/Technology 9:1373; Hoogenboom et al. (1991) Nuc Acid Res 19:4133; Barbas et al. (1991) PNAS 88:7978; McCafferty et al. Nature (1990) 348:552. Recombinant anti-OPN-c antibodies, such as chimeric and humanized monoclonal antibodies, comprising both human and non-human portions, which can be made using standard recombinant DNA techniques, are also disclosed. Such chimeric and humanized monoclonal antibodies can be produced by recombinant DNA techniques known in the art, e.g., using methods described in Robinson et al. PCT/US86/02269; Akira et al. EP Application 184,187; Taniguchi, EP Application 171,496; Morrison et al. EP Application 173,494; Neuberger et al. WO 86/01533; Cabilly et al. U.S. Pat. No. 4,816,567; Cabilly et al. EP Application 125,023; Better et al. (1988) Science 240:1041; Liu et al. (1987) PNAS 84:3439; Liu et al. (1987) J. Immunol. 139:3521; Sun et al. (1987) PNAS 84:214; Nishimura et al. (1987) Canc. Res. 47:999; Wood et al. (1985) Nature 314:446; Shaw et al. (1988) J. Natl Cancer Inst. 80:1553; Morrison, S. L. (1985) Science 229:1202; Oi et al. (1986) BioTechniques 4:214; Winter U.S. Pat. No. 5,225,539; Jones et al. (1986) Nature 321:552; Verhoeyan et al. (1988) Science 239:1534; Beidler et al. (1988) J. Immunol 141:4053.

As used herein, "antibody" includes fragments thereof that are also specifically reactive with OPNcPEP. As described above, the term OPNcPEP also includes derivatives and modifications including, for example, shorter (truncated) sequences, post-translationally modified sequences, such as phosphorylated, modified sequences, etc. Antibodies can be fragmented using conventional techniques and the fragments screened for utility in the same manner as described above for whole antibodies. For example, F(ab)$_2$ fragments can be generated by treating the antibody with pepsin. The resulting F(ab)$_2$ fragment can be treated to reduce disulfide bridges to produce Fab fragments. The disclosed antibody also includes bispecific and chimeric molecules having affinity for OPNcPEP conferred by at least one complementarity-determining regions (CDR) of the antibody.

Antibodies that specifically bind OPN-c epitopes can also be used in immunohistochemical staining of tissue samples to evaluate the abundance and pattern of expression of SEQ ID NO: 8. Anti-OPN-c antibodies can be used diagnostically in immuno-precipitation and immuno-blotting to detect and evaluate OPN-c peptide levels in tissue as part of a clinical testing procedure. Likewise, the ability to monitor OPN-c peptide levels in an individual can allow determination of the efficacy of a given treatment regimen for an afflicted individual. Diagnostic assays using anti-OPN-c antibodies can include, e.g, immunoassays designed to aid in early diagnosis of a degenerative disorder, such as ones manifest at birth. Diagnostic assays using anti-OPN-c polypeptide antibodies also include immunoassays designed to aid in early diagnosis and phenotyping neoplastic or hyperplastic disorders. The disclosed anti-OPN-c antibodies may also be used in immunological screening of cDNA libraries constructed in expression vectors such as λgt11, λgt18-23, λZAP, and λORF8. Messenger libraries of this type, having coding sequences inserted in the correct reading frame and orientation, can produce fusion proteins, e.g., λgt11 will produce fusion proteins whose amino termini consist of β-galactosidase amino acid sequences and whose carboxyl termini consist of a foreign polypeptide. Antigenic epitopes of an OPN-c peptide, e.g. other orthologs of a particular OPN-c peptide or other paralogs from the same species, can then be detected with antibodies as, e.g., reacting nitrocellulose filters lifted from infected plates with anti-OPN-c antibodies. Positive phage detected can then be isolated from the infected plate. Thus, the presence of OPN-c homologs can be detected and cloned from other animals, as can alternate forms (including splicing variants) from humans.

In embodiments, a label is attached to the antibodies to facilitate detection. One method for labeling an anti-OPN-c specific antibody is via linkage to an enzyme and use in an enzyme immunoassay (EIA) (Voller, The Enzyme Linked Immunosorbent Assay (ELISA), Diagnostic Horizons 2:1 (1978) Microbiological Associates Quarterly Publication, Walkersville Md.; Voller et al., J. Clin. Pathol. 31:507 (1978); Butler, Meth. Enzymol. 73:482 (1981); Maggio (Ed.) Enzyme Immunoassay, CRC Press, Boca Raton Fla. (1980); Ishikawa et al. (Eds.) Enzyme Immunoassay, Kgaku Shoin, Tokyo, 1981). The enzyme, which is bound to the antibody, reacts with an appropriate substrate, such as a chromogenic substrate, to produce a detectable chemical moiety e.g., by spectrophotometric, fluorimetric, or by visual means. Enzymes used to detectably label the antibody include, but are not limited to, malate dehydrogenase, staphylococcal nuclease, δ-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase, acetylcholinesterase, etc. Detection can be by colorimetric methods, which employ a chromogenic substrate for the enzyme, by visual comparison of the extent of enzymatic reaction of a substrate in comparison with similarly prepared standards, and/or by a variety of other immunoassays. For example, radioactively labeling the antibodies or antibody fragments allows detection of fingerprint gene wild type or mutant peptides through radioimmunoassay (RIA) (e.g., Weintraub, B., Principles of Radioimmunoassays, Seventh Training Course on Radioligand Assay Techniques, The Endocrine Society, March, 1986, which is incorporated by reference herein). The radioactive isotope can be detected by use of a γ-counter or a scintillation counter, or by autoradiography.

The antibody may also be labeled with a fluorescent compound that, when exposed to light of the proper wavelength, is detectable. Fluorescent labeling compounds include, but are not limited to, fluorescein isothiocyanate, rhodamine, phycoerythrin, phycocyanin, allophycocyanin, o-phthaldehyde, and fluorescamine. The antibody can also be detectably labeled using fluorescence emitting metals such as $^{152}$Eu or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound, and the presence of the chemiluminescent-tagged antibody is determined by detecting luminescence that arises during the course of a chemical reaction. Examples of chemiluminescent labeling compounds include, but are not limited to, luminol, isoluminol, theromatic acridinium ester, imidazole, acridinium salt, and oxalate ester. The antibody may also be labeled with a bioluminescent compound. Bioluminescence is a type of chemiluminescence found in biological systems, in which a catalytic protein increases the efficiency of the chemiluminescent reaction. The presence of a bioluminescent protein is determined by detecting the presence of luminescence. Bioluminescent compounds include, but are not limited to, luciferin, luciferase, and aequorin.

In one embodiment an OPN-c nucleic acid fragment is an oligonucleotide probe that specifically detects an OPN-c nucleic acid relative to another, related OPN nucleic acid. In one embodiment, the oligonucleotide hybridizes under stringent conditions to a nucleic acid with at least about 6 consecutive nucleotides encoding SEQ ID NO: 8. In one embodiments, the probe further contains a detectable label, e.g., a radioisotope, fluorescent compound, enzyme, biotin, enzyme co-factor, etc. Probes based on SEQ ID NO: 8 can detect transcripts or genomic sequences encoding the same or homologous proteins.

Kits are disclosed that contain reagents for use of antibodies against SEQ ID NO: 8 in diagnostic and therapeutic methods to specifically target OPN-c peptides SEQ ID NO: 8, truncation and/or modified forms of SEQ ID NO: 8 and/or their encoding nucleic acid sequences, e.g., SEQ ID NO: 36. In one embodiment, for diagnostic purposes, a kit detects the presence of OPN-c mRNA transcripts or the peptides they encode in a biological sample. The kit can include a probe (e.g., a nucleic acid sequence or an antibody), a standard and, optionally, instructions for use. More specifically, antibody-based kits can include a first antibody (e.g., in solution or attached to a solid support) that specifically binds OPN-c SEQ ID NO: 8, and, optionally, a second different antibody that specifically binds to the first antibody (i.e., anti-antibody) and is conjugated to a detectable agent (i.e., a label). In one embodiment, an oligonucleotide-based kit includes an oligonucleotide (e.g., a detectably labeled oligonucleotide) that hybridizes specifically to an OPN-c mRNA transcript under stringent conditions, such as a high annealing temperature. For example, the oligonucleotides can encode a sequence that bridges the exon 3/exon 5 junction to indicate the presence of OPN-c mRNA transcripts. The kit, optionally, can contain a mixture of oligonucleotides (such as two oligonucleotides as primers for PCR, or oligonucleotides that hybridize with OPN-c in conjunction with oligonucleotides that hybridize with a control sequence). The kits can contain reagents specific for, e.g., Northern blot analysis, for in situ hybridization, etc.

In one embodiment, a diagnostic kit also contains a triplet of oligonucleotides that can be used in RT-PCR analysis to amplify a nucleic acid sequence within OPN-c. One primer (e.g., an oligo(dT) primer, or a primer flanking a splice junction) is provided for reverse transcription of mRNA to synthesize cDNA. A pair of primers is provided to PCR amplify the OPN-c splice variants. For example, the primers can hybridize to or around the relevant OPN-c splice junction, within optional or common exons, or to the 5' and 3' untranslated sequences flanking the coding region.

In any embodiment, the kits can also include a buffering agent, a preservative, a protein-stabilizing agent, and/or a component(s) to detect any included label (e.g., enzyme, substrate, etc.). The kits can also contain a control sample or a series of control samples that can be assayed and compared to the test sample. Each component of the kit can be enclosed within an individual container, and all of the various containers can be within a single package.

The invention will be further appreciated with respect to the following examples.

EXAMPLE 1

Reverse transcription-PCR. A schematic of the structural characteristics of the OPN gene product is shown in FIG. 1A. The OPN gene SEQ ID NO: 2 has six translated exons and splice variants are generated by elimination of exons 4 (OPN-c SEQ ID NO: 6) or 5 (OPN-b SEQ ID NO: 4). There are two main domains on the protein that are separated by a protease-sensitive site, an N-terminal fragment encompassing the integrin binding domains, while the CD44v binding domain lies on the C-terminal part of the molecule. The integrin binding site covers the sequence GRGDS SEQ ID NO: 31. The smallest integrin $\alpha_v\beta_3$ binding peptide identified starts at amino acid 71. Binding to $\beta_1$-containing integrins occurs through the non-canonical sequence SVVYGLR SEQ ID NO: 32, unless the $\beta_1$ chain is paired with $\alpha_4$, in which case the binding site ranges from amino acid 131 to 144. The CD44v6 binding site covers the region from amino acid 169 to 220. Heparin-bridges between OPN and CD44v3 may be formed via the heparin binding sites on amino acids 170 and 300. The bases of the coding sequence and the corresponding amino acids are numbered such that the start site, or initiating methionine is 1 and the schematic is not drawn to scale.

Figure 1B:
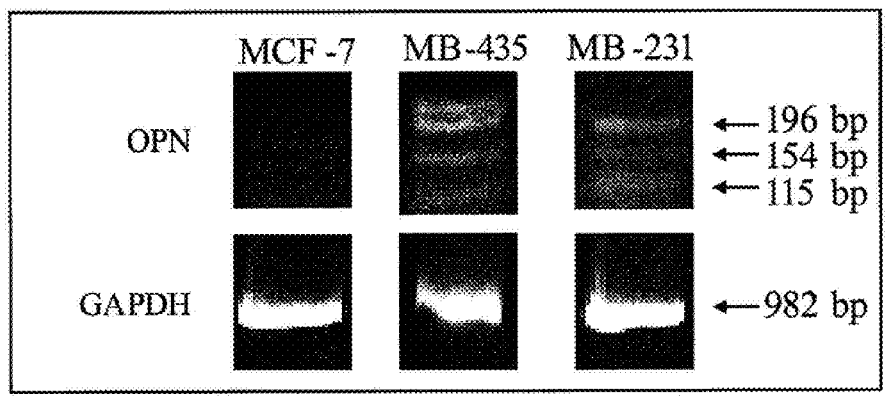
FIG. 1B shows expression of OPN ribonucleic acid (RNA) in various tumor cell lines

Cells were plated at $1 \times 10^5$/well in 24-well plates and allowed to adhere for seven hours before starvation in growth factor- and serum-deprived medium. Total RNA was extracted, reverse transcribed with oligo-dT and PCR was performed with primers that span the region from base pairs 50 to 246 with the primers 5'-TAC CAG TTA AAC AGG CTG ATT C-3' SEQ ID NO: 19 and 5'-CCA TAT CAT CCA TGT GGT CA-3' SEQ ID NO: 20. PCR of glyceraldehyde 3-phosphate dehydrogenase (GAPDH) was used as a control for the amount of template present. The slowest migrating band (no arrow) seen in MDA-MB-435 cells was often present in the no template control sample and was deemed to be non-specific. MCF-7 cells were non-invasive while MDA-MB-435 and MDA-MB-231 were metastatic. As seen in FIG. 1B, MCF-7 cells did not express OPN-c, while the metastatic cells did express a PCR product corresponding to OPN-c.

Figure 1C:
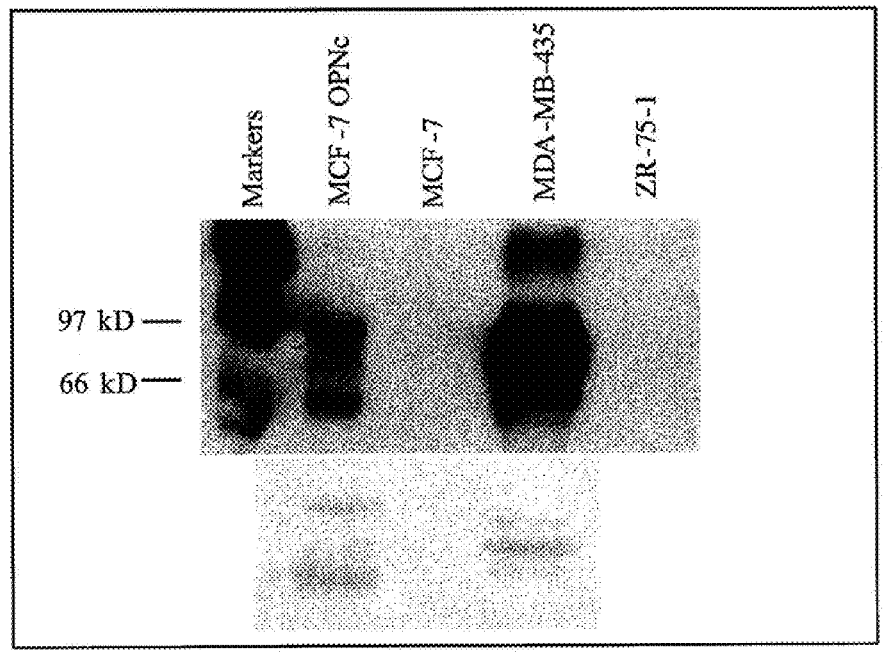
FIG. 1C shows expression of OPN protein in various tumor cell lines.

Western blotting to detect secreted OPN in cell culture supernatant is shown in FIG. 1C. ZR75-1 and MCF-7 are non-invasive, breast tumor cell lines and they do not express OPN proteins. MDA-MB-435 cells are malignant, breast cancer cells, which contain RNA messages for all three forms of OPN (as shown in FIG. 1B) and consistently express three protein forms of OPN as seen on Western blotting of supernatant of MDA-MB-435 cells. MCF-7 cells were stably transfected with OPNc SEQ ID NO: 6. Supernatant from MCF-7 cells transfected with OPN-c SEQ ID NO: 6 was loaded as a positive control. The lower panel shows a low exposure to demonstrate the separation of 3 bands in the MDA-MB-435 supernatants.

Figure 1D:
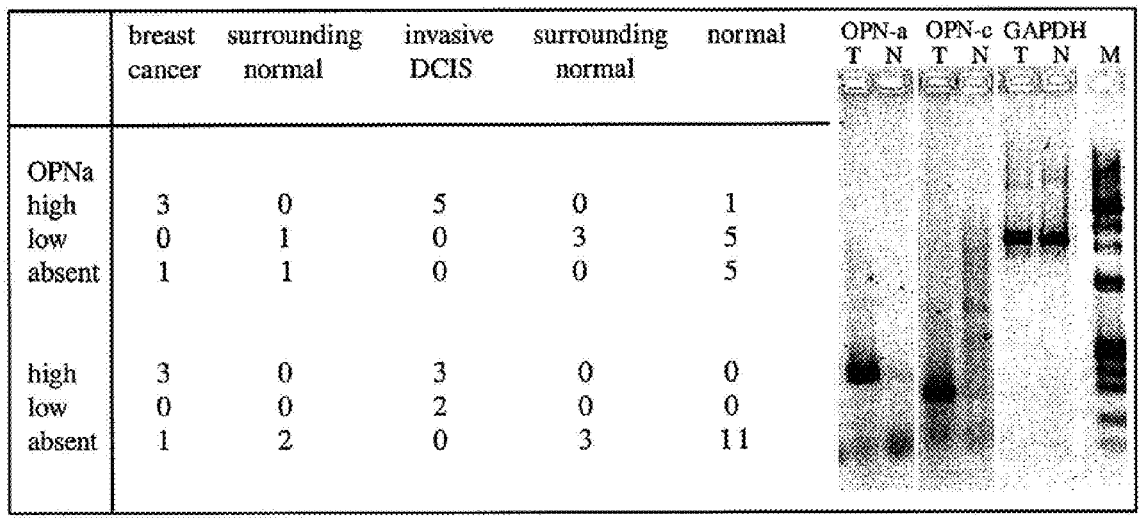
FIG. 1D shows expression of OPN in breast specimens.

Expression of OPN-a SEQ ID NO: 2 and OPN-c SEQ ID NO: 6 in human breast tissue specimens was assessed by RT-PCR as shown in FIG. 1D. Amplification of GAPDH provided a control for template integrity and abundance. Total RNA was extracted from human tissues using TRIZOL® (1 ml reagent/200 mg tissue) according to the manufacturer's protocol. Three micrograms of total RNA was reverse transcribed by SuperScript II RNase H reverse Transcriptase (Invitrogen, Carlsbad Calif.). The OPN splice variants -a and -c were amplified with the primer pairs 5'-ATCTCCTAGC-CCCACAGAAT-3' (forward) SEQ ID NO: 9 and 5'-CATCA-GACTGGTGAGAATCATC-3' (reverse) SEQ ID NO: 10 for OPN-a and 5'-CTGAGGAAAAGCAGAATG-3' (forward) SEQ ID NO: 11 and 5'-AATGGAGTCCTGGCTGT-3' (reverse) SEQ ID NO: 12 for OPN-c. Amplification of GAPDH with primers 5'-TGAAGGTCGGAGTCAACGGATTTGGT-3' (forward) SEQ ID NO: 13 and 5'-CATGTGGGCCAT-GAGGTCCACCAC-3' (reverse) SEQ ID NO: 14 served as a control for equal loading and integrity of the cDNA. A 35 cycle touchdown PCR, with Taq DNA Polymerase and at 1.5 mM $MgCl_2$, was performed with 5 cycles at 59° C. annealing temperature, 5 cycles at 55° C. annealing temperature, and 25 cycles at 51° C. annealing temperature. All PCR products were analyzed by Tris-acetate EDTA agarose (2.5% w/v) gel electrophoresis. To confirm the specificity of the primer pairs for OPN-a and OPN-c, their PCR products from a representative tumor sample were cloned and sequenced. According to the intensity of the resulting band on agarose gel, the expression levels were rated as high, low, or absent. The numbers of specimens in each group are indicated. The panel to the right shows the RT-PCR results for a representative invasive DCIS (ductal carcinoma in situ) sample (T) and its surrounding normal tissue (N), M=size markers.

EXAMPLE 2

Real-time RT-PCR. Specimens of human breast tumors, non-transformed surrounding tissue, and healthy breast tissue obtained from reduction mammoplasties were provided by the tissue procurement facility of the University of Cincinnati Medical Center/Children's Hospital. Total RNA was extracted from specimens using TRIZOL® Reagent (Invitrogen) according to standard protocol. Total RNA was used for cDNA synthesis by reverse transcription using Superscript II (Invitrogen) according to manufacturer's protocol in a total volume of 20 µl. Primer sets for OPN were designed to distinguish the splice variants. Primer sets (Table 1) for CK-19, β-actin and aP-2 were from two express OPN-a and the splice variants -b and -c (He et al. Oncogene 2006;25:2192), were used as controls for calculating expression of OPN forms in the tissue. Where necessary, the PCR products were separated on agarose gel to confirm the correct size of the resulting band and the absence of primer dimers.

Figure 2:
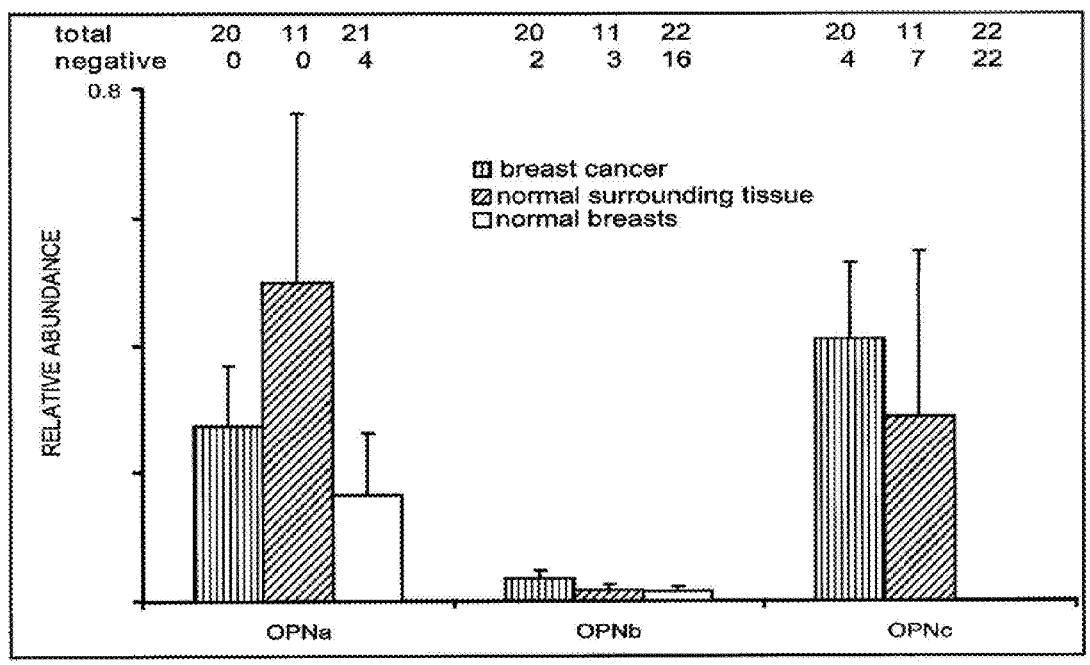
FIG. 2 shows the quantification of the RNA levels for three OPN variants in breast specimens.

Results are shown in FIG. 2. Amplification of OPNa, OPNb, and OPNc from breast cancers, surrounding normal tissues, and healthy controls (mean±SEM) are shown. The numbers are adjusted for the fraction of epithelial cells

TABLE 1

Primers and PCR Conditions

| Target sequence | Primer | Sequence | Product size (bp) | $[Mg^{2+}]$ (mM) | Annealing (° C.) |
|---|---|---|---|---|---|
| OPN-a | forward | SEQ ID NO: 9<br>5'-ATCTCCTAGCCCCACAGAAT-3' | 208 | 2.5 | 58 |
|  | reverse | SEQ ID NO: 10<br>5'-CATCAGACTGGTGAGAATCATC-3' |  |  |  |
| OPN-b | forward | SEQ ID NO: 21<br>5'-ATCTCCTAGCCCCAGAGAC-3' | 209 | 2.5 | 62 |
|  | reverse | SEQ ID NO: 22<br>5'-AAAATCAGTGACCAGTTCATCAG-3' |  |  |  |
| OPN-c | forward | SEQ ID NO: 23<br>5'-TGAGGAAAAGCAGAATGCTG-3' | 155 | 3.0 | 62 |
|  | reverse | SEQ ID NO: 24<br>5'-GTCAATGGAGTCCTGGCTGT-3' |  |  |  |
| β-Actin | forward | SEQ ID NO: 25<br>5'-GGCGGCACCACCATGTACCCT-3' | 200 | 2.0 | 65 |
|  | reverse | SEQ ID NO: 26<br>5'-AGGGGCCGGACTCGTCATACT-3' |  |  |  |
| Ck-19 | forward | SEQ ID NO: 27<br>5'-CCCGCGACTACAGCCACTA-3' | 163 | 2.0 | 60 |
|  | reverse | SEQ ID NO: 28<br>5'-CTCATGCGCAGAGCCTGTT-3' |  |  |  |
| aP2 | forward | SEQ ID NO: 29<br>5'-TCAGTGTGAATGGGGATGTG-3' | 249 | 1.6 | 58 |
|  | reverse | SEQ ID NO: 30<br>5'-GTGGAAGTGACGCCTTTCAT-3' |  |  |  | different exons to avoid amplification of contaminating genomic DNA. All PCR reactions were performed on a Cepheid (Sunnyvale Calif.) Smart Cycler using SYBR Green detection format. 0.5 µl of cDNA was used for each PCR reaction in a total volume of 25 µl. Standard Invitrogen PCR buffer system was used and the amount of $MgCl_2$ optimized for each set of primers. For each experiment a no-template reaction was included as a negative control. Conditions for PCR were 94° C. denaturation for 120 s followed by 35-40 cycles of 94° C. melting for 15 s, a primer set specific annealing temperature, extension at 72° C. and melting curve program (60-95° C. with a heating rate of 0.2° C. and a continuous fluorescence measurement), and finally a cooling step to 40° C. Product purity was confirmed by DNA melting curve analysis and agarose gel electrophoresis. In some cases, amplification of primer dimers was observed in no-template reaction at later cycles. Melt curves yielded a single sharp peak for all template reactions, and minimal melt peak (for primer dimers) or no melt peaks for the no-template control reactions. PCR efficiencies were determined for given primer sets, by cDNA dose-response curve analysis. β-actin was used as a reference gene. Relative expression ratio of the target gene was calculated from the cycle threshold and efficiency measurements. MDA-MB-435 cells, known to according to markers for epithelia and adipocytes. Total number of samples tested and the number of specimens with undetectable OPN RNA are indicated above the graph.

EXAMPLE 3

DNA constructs and transfection. Constructs for expression of the human OPN splice variants were obtained by reverse transcription-PCR from the malignant breast tumor cell line MDA-MB-435. Total RNA was isolated sing RNeasy mini kit (Qiagen, Valencia Calif.) following the manufacturer's protocol. One microgram of total RNA was used for cDNA synthesis with Super-script II RNase H reverse transcriptase (Gibco BRL, USA). The coding sequence of OPN was amplified with the primers 5'-CAA ACG CCG ACC AAG GGA AAA C-3' SEQ ID NO: 15 and 5'-CTT CTT TCT CAG TTT ATT GGT-3' SEQ ID NO: 16. The amplified product was TA cloned, excised with Xho1 and Nhel, and was subcloned into the vector pCR3.1 (Invitrogen). Genes cloned into this vector are expressed under control of the CMV promoter. Sequence fidelity and accurate reading frame were verified by DNA sequencing analysis. MCF-7 cells were transfected using FuGene® (Roche Diagnostics), and stable clones were selected in G418, as shown in FIG. 3.

To generate GST-OPN fusion proteins, OPN cDNAs were amplified by PCR by exclusion of the signal peptide (1-17 amino acids) with the primers 5'-c ggg atc ccc ATA CCA GTT AAA CAG GCT GAT-3' SEQ ID NO: 17 and 5'-gg ctc gag ATG TTC TCT TTC ATT TTG CTA-3' SEQ ID NO: 18 using pCR3.1-OPNs as templates (lower case letters show BamH I and Xho I sites and protective bases to facilitate cloning). Amplified fragments were subcloned into a pGEX-5T vector and transformed into BL21 bacteria for making GST-OPN fusion proteins. The OPNc sequence thus fused downstream to the GST sequence comprises SEQ ID NO: 40. Reading frames and sequence fidelity were confirmed by sequencing analysis.

Figure 3A:
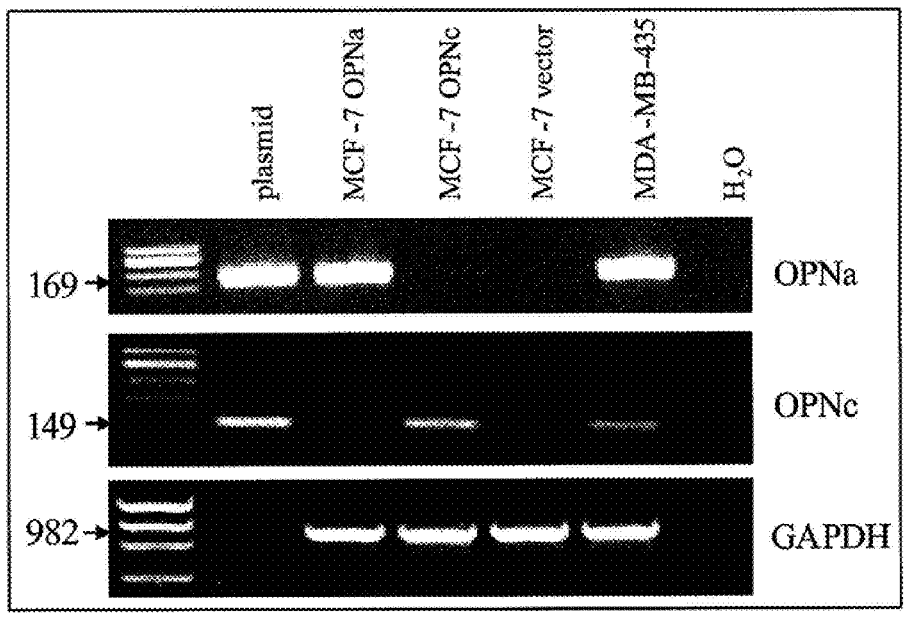
FIGS. 3A, 3B, and 3C show the expression of the OPN variants -a and -c in a cell line that does not express endogenous OPN and the expression and purification of GST-OPN forms in bacteria.
Figure 3B:
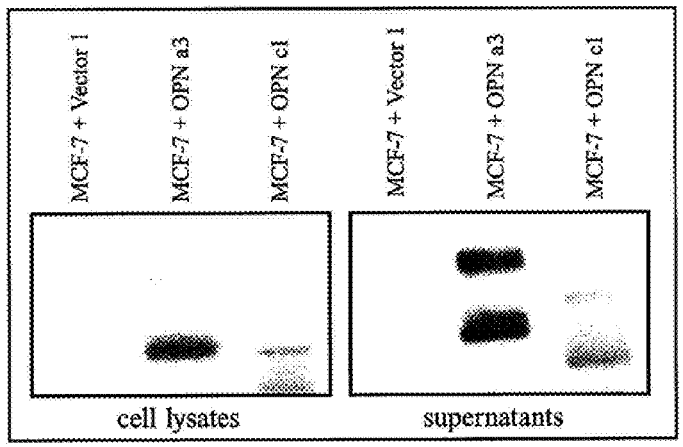
Figure 3C:
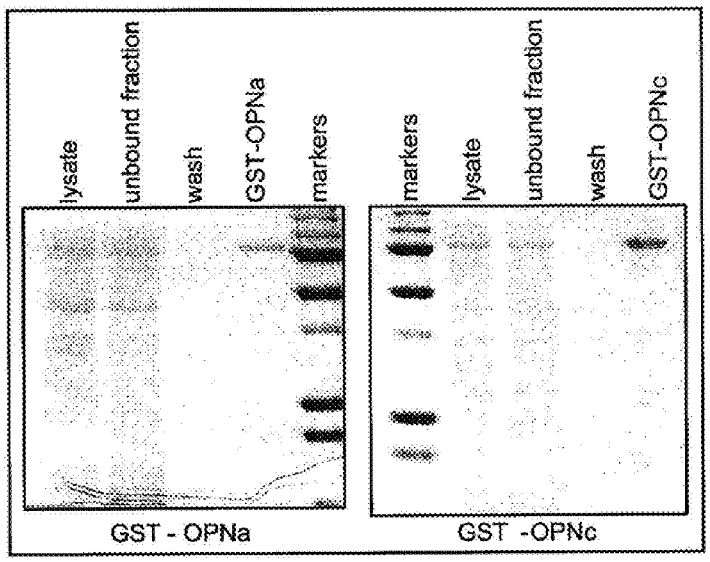

As shown in FIG. 3, RNA expression according to RT-PCR with primers specific for the splice variants OPN-a or OPN-c (upper panel). The housekeeping gene GAPDH served as a positive control. OPN splice variants -a and -c were stably transfected into MCF-7 breast tumor cells. Clones were selected and starved in serum-free medium for fourteen hours. OPN levels were measured by Western blotting on cell lysates (20 μg/lane) and supernatants (40 μl/lane) as shown in the middle panel. Secondary antibody alone did not produce any signal (not shown). Additional stably expressing clones were selected and used in confirmatory experiments (not shown). OPN-a and -c were amplified by PCR by exclusion of the signal peptide (1-17 amino acids). The amplified fragments were subcloned into pGEX-5T vector and transformed into BL21 bacteria for making GST-OPN fusion proteins. Reading frames and sequence fidelity were confirmed by sequencing analysis. The proteins were purified from bacterial lysates by pull-down with GSH-Sepharose as shown in the lower panel. Their identity as OPN was confirmed by Western blotting (not shown).

EXAMPLE 4

Colony formation in soft agar. MCF-7 cells and MDA-MB-435 cells were grown in α-MEM with insulin and 10% fetal bovine serum. The metastatic breast cancer cell line MDA-MB-231 (ATCC HTB-26) was grown in α-MEM with 10% FBS. ZR-75-1 (ATCC HTB-22) cells, derived from a ductal carcinoma, were tumorigenic but non-metastatic. They were grown in RPMI with 10% fetal bovine serum. The anti-OPN antibody O-17 without azide (Assay Designs Inc.) was used in the soft agar assay.

Cells ($1 \times 10^5$ cells per 60-mm dish) were plated in triplicates with a top layer of 0.3% agar (BACTO Agar, Difco, Detroit Mich.) and a bottom layer of 0.5% agar (both in α-MEM). Every other day, 0.4 ml of medium was supplemented and the plates were examined microscopically for growth. After one week, photographs were taken at high and low magnification and the surface area of all clones in five fields was measured with the imaging software ImageJ (NIH) or Metamorph. OPN expression levels on the day of plating were confirmed by Western blotting.

Figures 4A, 4B:
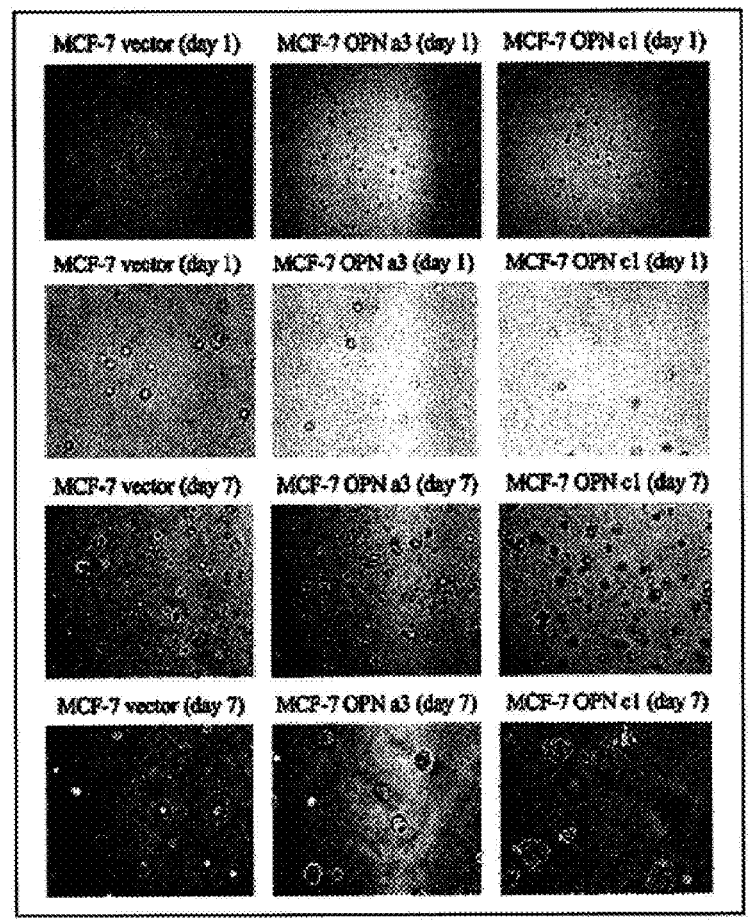
FIGS. 4A, 4B, 4C, and 4D show the effects of OPNa and OPNc on soft agar clone formation by MCF-7 breast tumor cells.
Figure 4C:
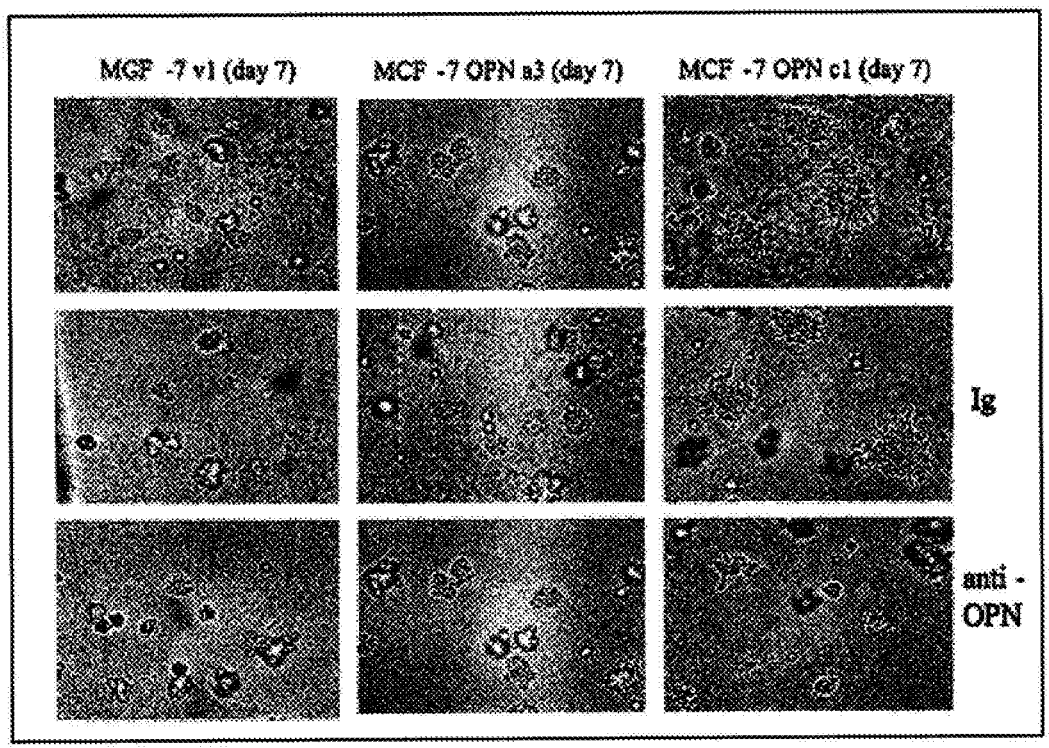
Figure 4D:
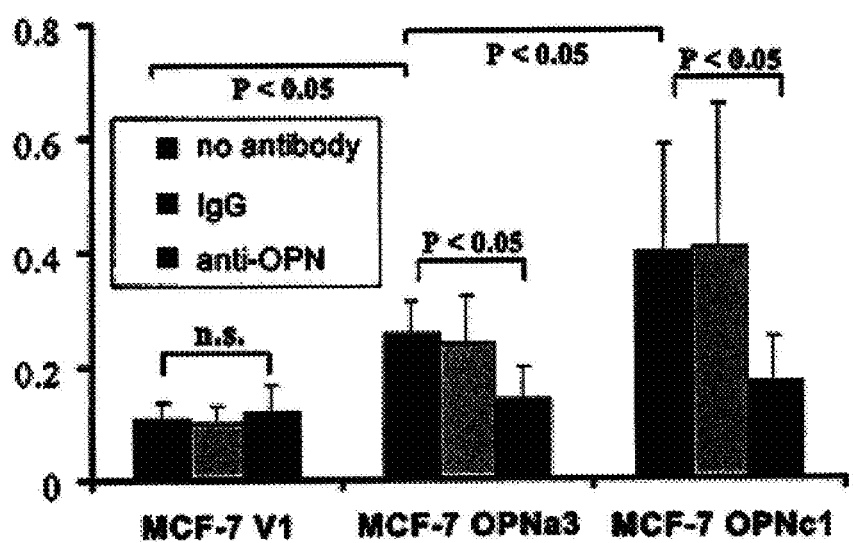
Figure 5A:
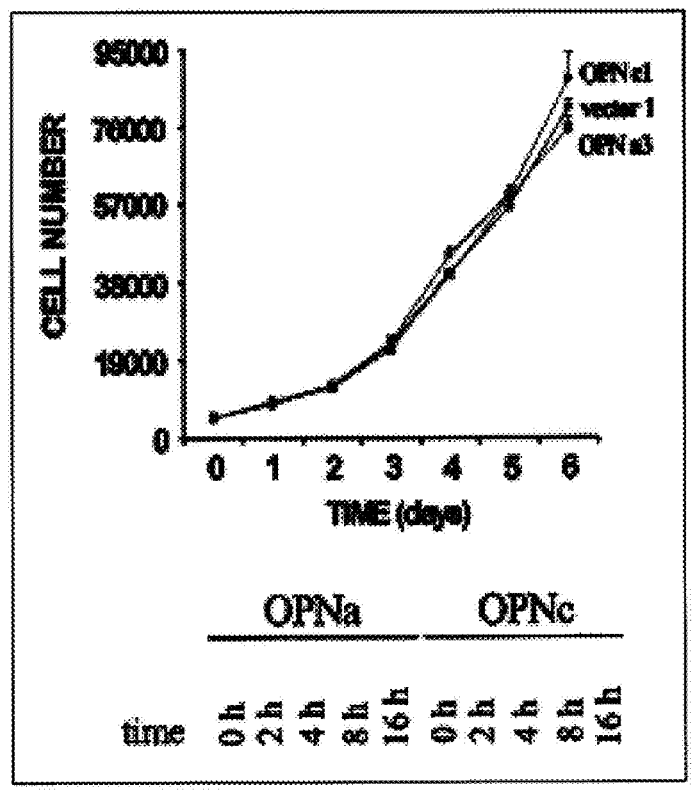
FIGS. 5A, 5B, 5C, 5D, 5E, 5F, and 5G show the effects of OPNa and OPNc on cell growth and cell adhesion, as well as the aggregation of OPN variants in the presence of calcium.
Figure 5B:
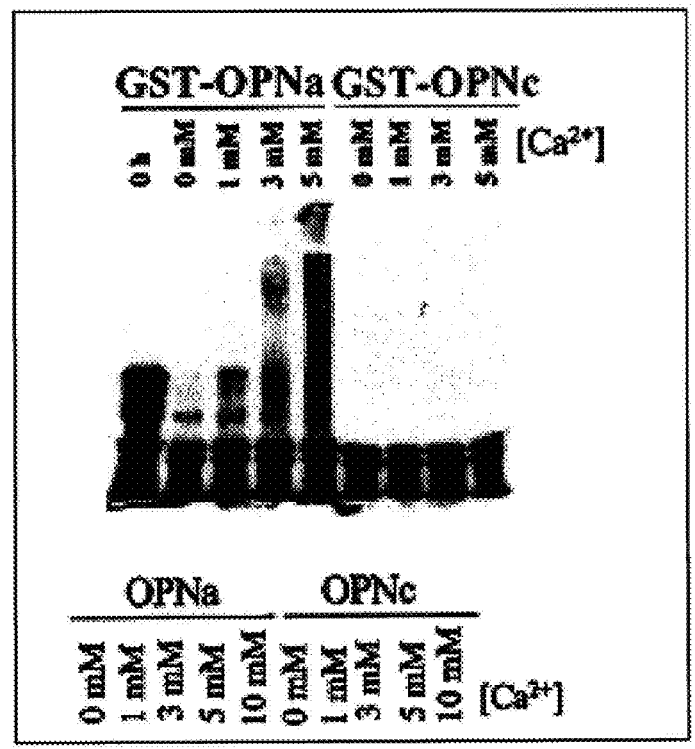
Figure 5C:
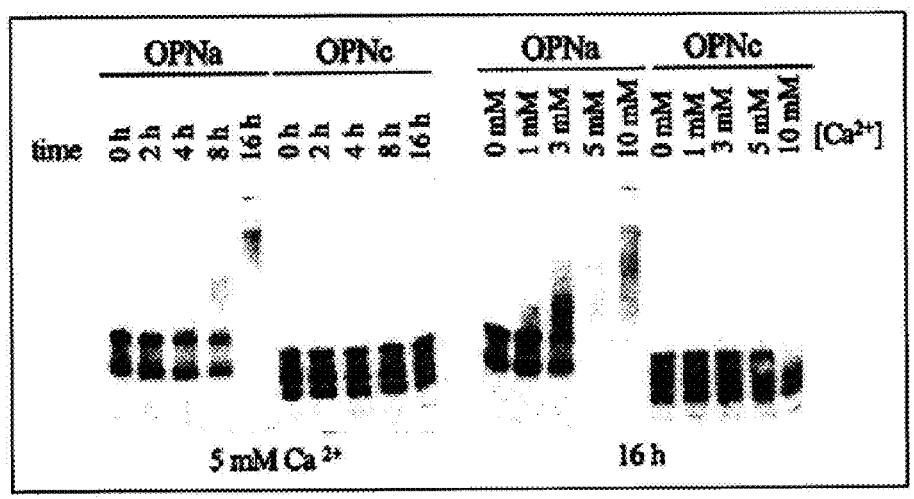
Figure 5D:
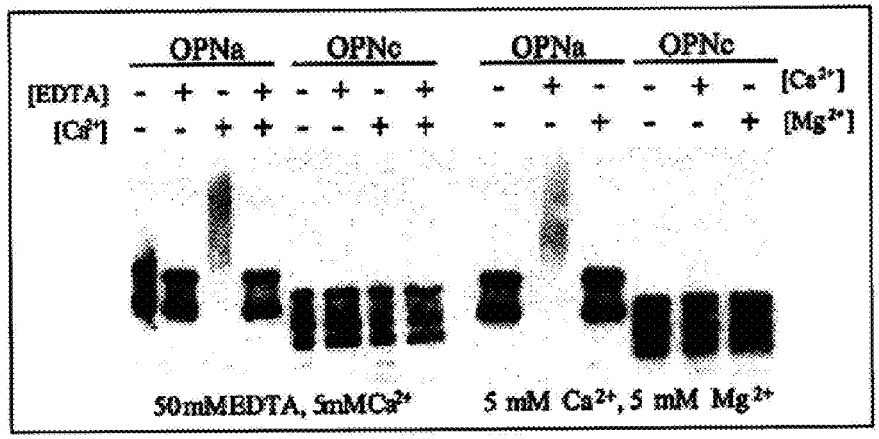
Figure 5E:
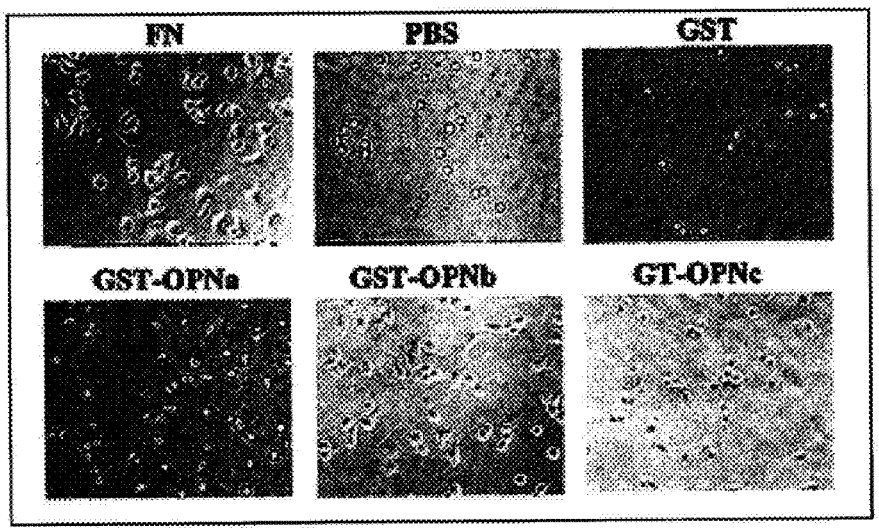
Figure 5F:
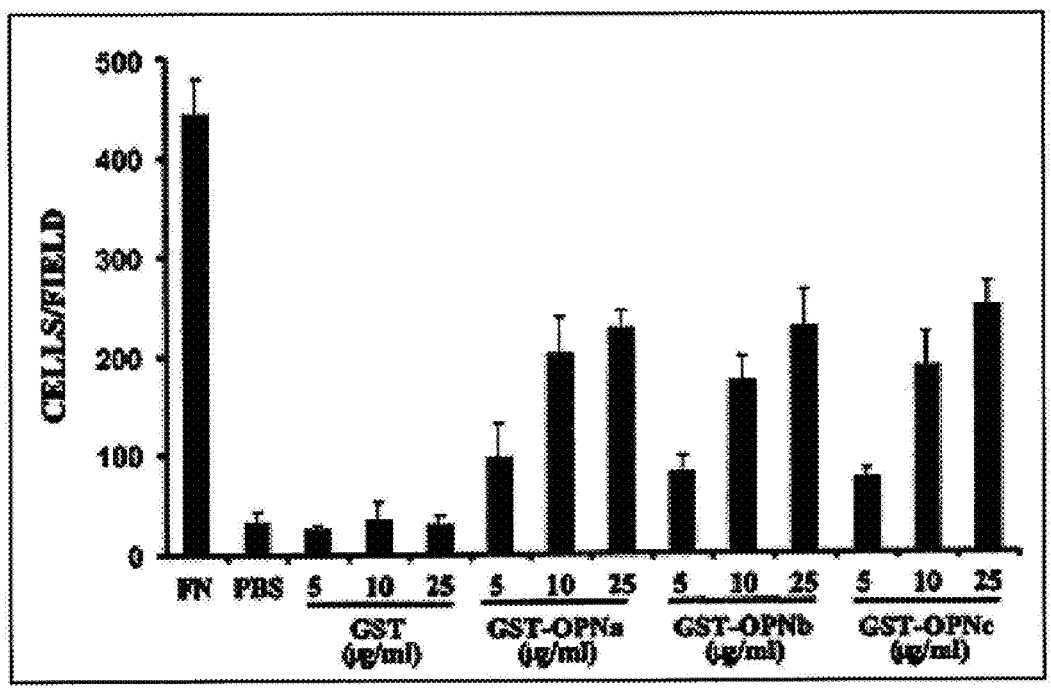
Figure 5G:
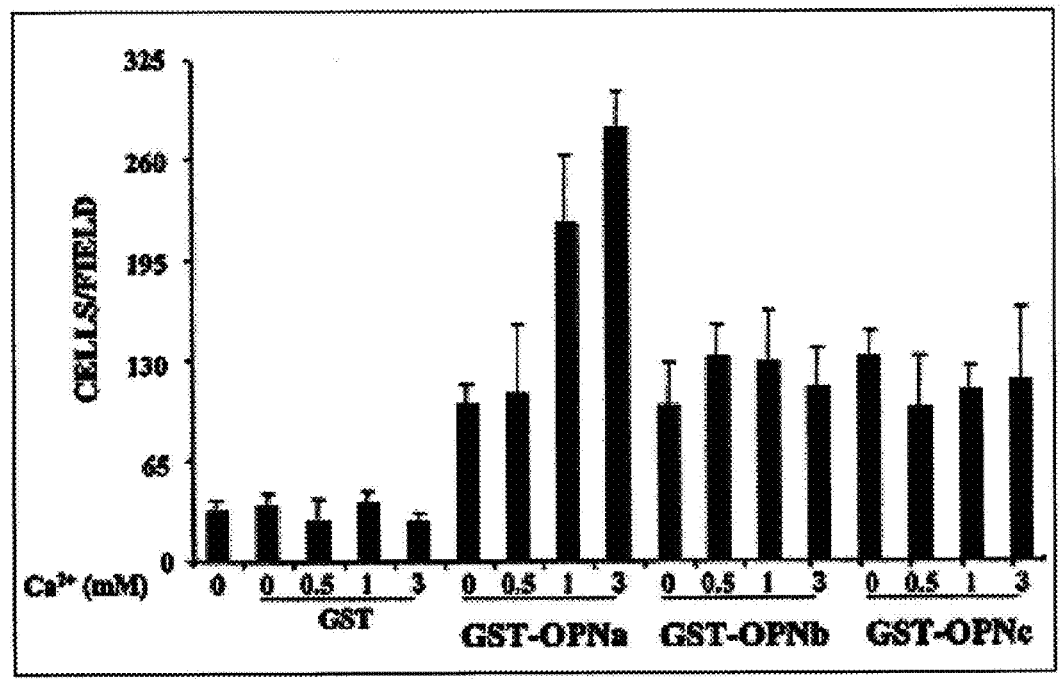

Results are shown in FIG. 4. Photomicrographs were taken on days 1 (top panels) and 7 (bottom panels) after plating at low magnification (to show clone frequency) and at large magnification (to show clone size and shape). Protrusions from the clones formed were visible in MCF-7 OPNc1, but not in the MCF-7 cells transfected with OPN-a (MCF-7 OPNa3) or in the vector control (MCF-7 v1), as shown in FIG. 4A. The combined data from three experiments were evaluated to determine the average clone size (relative units) and clone frequency, formed by MCF-7 cells transfected with vector, OPN-a, or OPN-c. Five fields per plate were photographed and all clones in focus were measured, as shown in FIG. 4B. The table shows the mean and range of all measured clones (indicated as n). The differences among the groups in clone size, but not in clone frequency, were statistically significant according to the t-test. FIG. 4C shows soft agar colony formation by transfected MCF-7 cells in the absence of antibody (top panel) or with addition every other day of anti-OPN antibody at 0.5 μg/ml in 0.3 ml medium (bottom panel) or rabbit IgG (Sigma) as immunoglobulin control (middle panel). FIG. 4D shows quantification of the average clone size; data represent mean±standard deviation. The data sets were analyzed for statistically significant differences by the U-test (Wilcoxon, Mann, and Whitney) and the t-test. The clone sizes for MCF-7 OPN-a and MCF-7 OPN-c were statistically significantly different from the clone sizes of MCF-7 vector and from one another.

EXAMPLE 5

Growth rates, aggregation, and adhesion. For investigation of cell growth rates, each cell line was plated at 5000 cells/well in 24-well plates. Daily, five wells per group were harvested by trypsinization and the cell numbers were determined in a Coulter™ Z-Series Counter. At each time point, the cell numbers from the five wells of the various groups of transfectants were analyzed for statistically significant differences (Wilcoxon-Mann-Whitney test and t-test), probability of error less than 5%.

To test aggregation, 40 μl supernatant from vector or OPN-a or OPN-c stable transfectants were incubated at 37° C. for indicated time in aggregation buffer (0.2 M NaCl, 0.05 M Tris-HCl, pH 7.6, 5 mM $CaCl_2$ final concentration) or at various $Ca^{2+}$ concentrations for 16 h. Samples were resolved on reducing denaturing SDS/polyacrylamide gels and transferred to PVDF membranes followed by Western blotting.

96-well polystyrene plates were coated with the indicated amounts of GST-OPN forms or control fibronectin (50 μ/ml) in 100 μ/well at 4° C. overnight. The wells were washed twice with cold PBS followed by blocking with 1% BSA for 1 h at 37° C. MCF-7 parental cells were used to assay adhesion. Cells were trypsinized and treated with soybean trypsin inhibitor, then washed twice with PBS and resuspended in adhesion buffer (0.1% BSA, 1 mM sodium pyruvate, 2 mM $MgCl_2$). Cells ($2 \times 10^4$ cell/well) were added to the above 96-well plates and allowed to adhere at 37° C. for two hours. Non-adherent cells were removed by rinsing twice with PBS. Adherent cells were counted and photographed. For adhesion to aggregated OPN, 1 μg of GST or GST-OPN forms were added to 96-well plated in aggregation buffer (0.2 M NaCl, 0.05 M Tris-HCl, pH 7.6, 5 mM $CaCl_2$ final concentration) and incubated at 4° C. overnight. All adhesion assays were performed with triplicate wells and were repeated at least three times.

Results are shown in FIG. 5. The expression of OPN splice variants did not affect the growth rate of MCF-7 cells, as shown in FIG. 5A. Stably transfected cells were plated at 5000 cells/well (24-well plate) on day 0. On every consecutive day, five wells per cell line were harvested and the total number of cells was counted. The Wilcoxon test and t-test did not indicate statistically significant differences among the data sets. As shown in FIG. 5B, purified bacterial recombinant GST-OPN-a aggregates in the presence of calcium, while GST-OPNc does not. Aggregation was assessed after 16 hours at increasing calcium concentrations. Consecutively denaturing, non-reducing SDS-PAGE and Western blotting for OPN was performed. FIG. 5C shows supernatants from MCF-7 cells transfected with OPN-a or OPN-c that were incubated for increasing time periods at 5 mM calcium (left panel) or with increasing amounts of calcium for 16 hours (right panel). FIG. 5D shows the need for calcium for OPN-a aggregation by reversal with 50 mM EDTA (left panel) or substitution with 5 mM magnesium (right panel). FIGS. 5E and 5F show the adhesion of MCF-7 cells to OPN splice variants. The wells of a 96-well plate were coated with GST-OPNs overnight. MCF-7 cells were allowed to adhere for 2 hours at 37° C. FIG. 5E shows microscopic pictures of the adhered cells after washing of the wells reflect cell spreading on plastic coated with fibronectin (FN) or GST-OPN, but not in the PBS control or in the well coated with GST. FIG. 5F shows the number of cells adhered to wells coated with increasing amounts of GST-OPN. Fibronectin (FN) served as positive control and PBS as negative control. FIG. 5G shows the adhesion of MCF-7 cells to 10 µg/ml of purified GST-OPN fusion proteins, after coating of the wells in the presence of increasing amounts of calcium (O-3 mM).

EXAMPLE 6

Induction of the expression of oxidoreductases and NF-κB. MCF-7 transfectants were plated in soft agar, following confirmation of their OPN expression by Western blotting. After seven days of soft agar growth, clone sizes were measured and RNA was extracted with 2 ml TriReagent LS. Linear amplification was performed with the Amino Allyl MessageAmp II kit (Ambion, Austin, Tex.), and samples were subjected to microarray analysis comparing MCF-7 OPN-c, MCF-7 OPNa, and MCF-7 vector. For each comparison, several hybridizations (4 for OPN-c versus OPNa and 2 each for OPNa versus vector and OPN-c versus vector) were performed with RNA from distinct soft agar plates and dye-flip of the fluorescent labels (http://microarray.uc.edu). The human 70-mer oligonucleotide library version 2.0 (21,329 optimized oligos) (Qiagen, Alameda Calif.) were printed on aminosilane-coated slides (Cel Associates, Inc., Pearland Tex.). Fluorescence-labeled cDNAs (Cy3 and Cy5; Amersham, Piscataway N.J.) for hybridization were synthesized from linearly amplified total RNA using an indirect amino allyl labeling method via an oligo(dT)-primed, reverse transcriptase reaction. Data representing background-subtracted spot intensities were analyzed after log-transformation and data centering.

Statistical significance of differential expression was assessed according to p-values, and adjusting for multiple hypotheses testing by calculating False Discovery Rates (FDR). Estimates of fold-change were calculated, and the cutoff used for significance was a fold change of >2, an intensity of >100, and an FDR<0.05. Significantly changed transcripts were tested against functional assignments, to determine which gene categories were enriched with differentially expressed genes, performed with Expression Analysis Systematic Explorer (EASE), using the gene categories of the Molecular Function and Biological Process branches of the Gene Ontology database (a multi-organism, controlled vocabulary database containing three separate ontologies: biological process, molecular function, and cellular component, commonly used for assessing results of microarray analyses). Fisher's Exact Probability, using the Benjamini FDR adjustment, was calculated for each gene category.

Figure 6B:
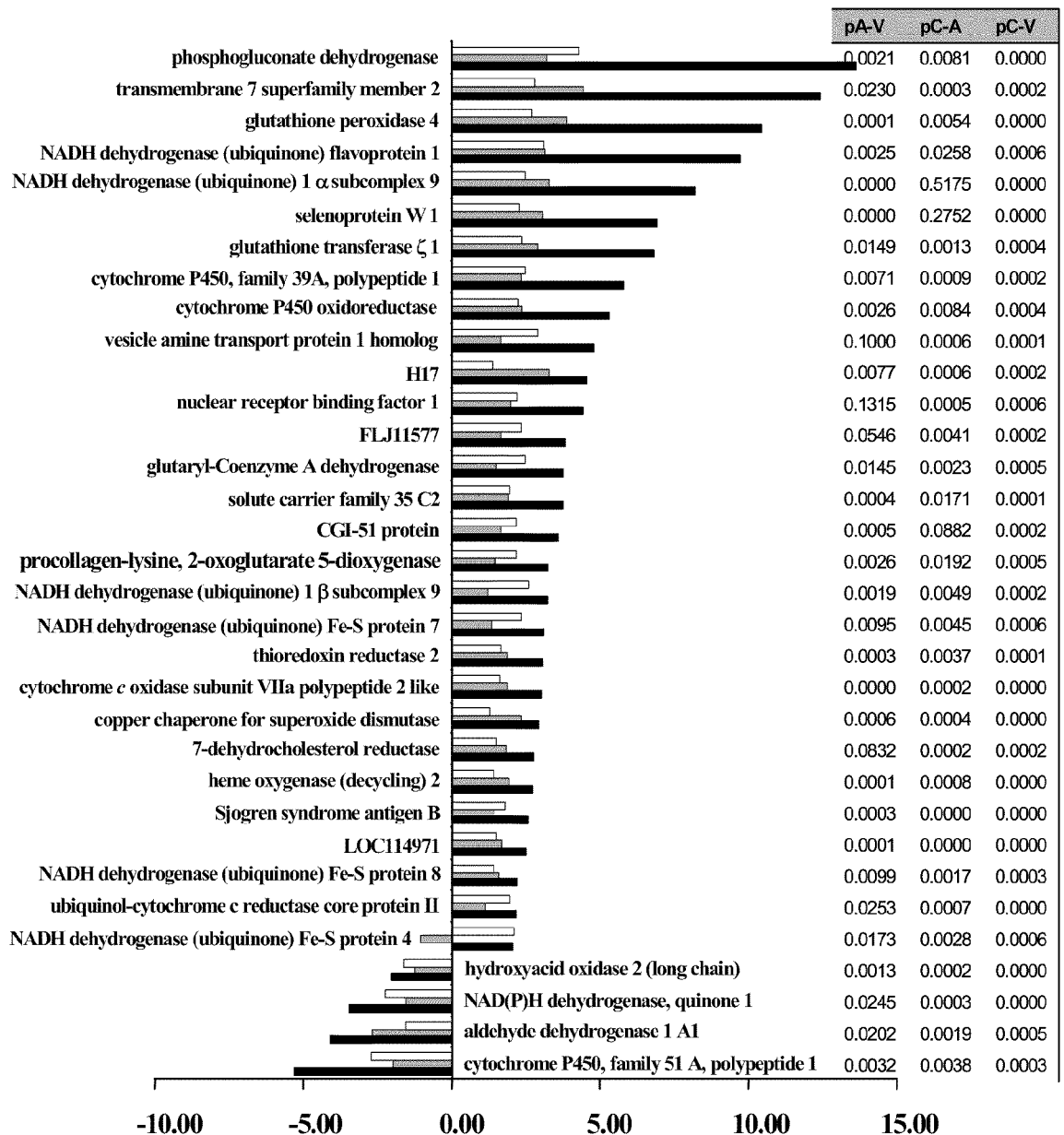

Results are shown in FIG. 6. Alterations in gene expression profiles were induced by OPN-c SEQ ID NO: 6 and OPN-a SEQ ID NO: 2 in soft agar. Cellular RNA was extracted from soft agar after seven days, and subjected to linear amplification, cDNA synthesis and dye labeling for microarray analysis of MCF-7 OPNc compared to MCF-7 vector, MCF-7 OPNc compared to MCF-7 OPNa, and MCF-7 OPNa compared to vector. FIG. 6A shows the genes that were significantly altered (p<0.005) by OPN-c SEQ ID NO: 6 as compared to vector, according to EASE analysis. The Genbank accession numbers in italics are also detected as altered in the EASE analysis of OPN-c SEQ ID NO: 6 versus OPN-a SEQ ID NO: 2. FIG. 6B shows the fold differences in expression within the groups of genes identified as significant in the EASE analysis for OPN-c SEQ ID NO: 6 versus vector (filled bars), OPN-c SEQ ID NO: 6 versus OPN-a SEQ ID NO: 2 (gray bars), and OPN-a SEQ ID NO: 2 versus vector (open bars). The panels to the right indicate the p values for significantly different expression of the individual genes (A-V=comparison of OPN-a to vector, C-A=comparison of OPN-c to OPN-a, C-V=comparison of OPN-c to vector).

Microarray results were validated by real-time PCR using a Cepheid Smart Cycler and a SYBR Green detection format. Oligo-dT primed first strand cDNA was synthesized using Invitrogen SuperScript according to the manufacturer's protocol. The PCR reaction contained 0.5× SYBR Green (Roche Diagnostics), $MgCl_2$ and primer concentrations were optimized for each gene. A 40 cycles PCR protocol consisted of 94° C. melting for 15 s, specific annealing for 30 s, and 20 s extension at 72° C. Melt curves yielded a single peak in all cases with no primer dimers. A no-template control was included in all reactions.

Genes selectively induced by OPN-c SEQ ID NO: 6 were identified. The stress-inducible transcription factor NF-κB frequently plays critical roles in the regulation of programmed cell death, which may be protective. While OPN has been known to induce the activity of NF-κB, there have not been reports of OPN-dependent gene expression of NF-κB family members. GenMAPP analysis of microarray data indicated that OPN-c SEQ ID NO: 6, but not OPN-a SEQ ID NO: 2, induced changes in the NF-κB pathway. Specifically, OPN-c SEQ ID NO: 6, but not OPN-a SEQ ID NO: 2, increased expression levels of both DNA binding NF-κB subunits p50 (and its precursor p105) and p65 (p<0.05 in comparing OPN-c SEQ ID NO: 6 versus vector, and OPN-c SEQ ID NO: 6 versus OPN-a SEQ ID NO: 2). Increased expression levels of NE-KB p65/p50 may protect breast cancer cells from anoikis (cell death caused by loss of adhesion) after induction selectively by OPN-c.

Figure 7A:
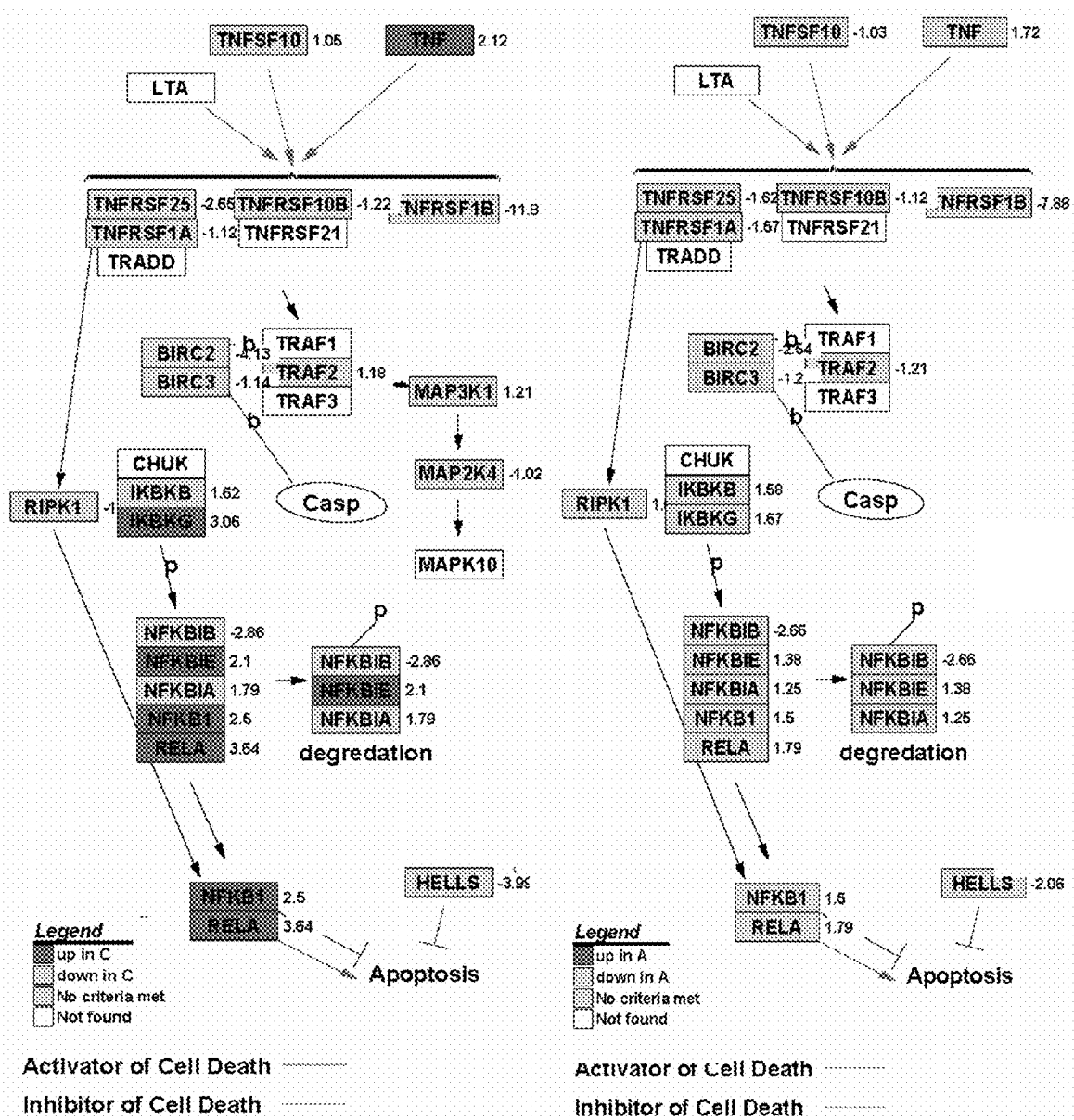

Alterations in NE-KB gene expression induced by OPN-c SEQ ID NO: 6 and OPN-a SEQ ID NO: 2 in soft agar are shown in FIG. 7. The microarray data were analyzed by GenMAPP for OPN-c-dependent expression changes (left) and for OPN-a-dependent changes in expression (right) of genes that regulate apoptosis pathways as compared to vector transfectants (FIG. 7A). FIG. 7B shows the fold differences in expression of NF-κB genes that were altered significantly (P<0.05, highlighted) in the comparison of OPN-c SEQ ID NO: 6 and vector. The panel to the right indicates the p values for significantly different expression of the individual genes (A-V=comparison of OPN-a to vector, C-A=comparison of OPN-c to OPN-a, C-V=comparison of OPN-c to vector).

EXAMPLE 7

Antibody specific to peptide at the OPN-c splice junction. A peptide identical the sequence around the splice site in OPN-c was synthesized: Ac-SGSSEEKQNAVSSEETC SEQ ID NO: 41. The C-terminal cysteine, not part of OPN-c, was used for coupling the peptide to the immunogen KLH. The antibody, raised in chickens, was an IgY purified from eggs and then affinity purified according to its binding to the immobilized peptide Ac-SGSSEEKQNAVSSEETC SEQ ID NO: 41, with the cysteine coupled to Sepharose beads. When used in immunohistochemistry, the antibody specifically stained breast cancers. Staining intensity was comparable to probing done with the pan-OPN antibody O-17. Normal breast tissue did not show substantial staining with either O-17 or the anti-OPN-c antibody (not shown).

Figure 8A:
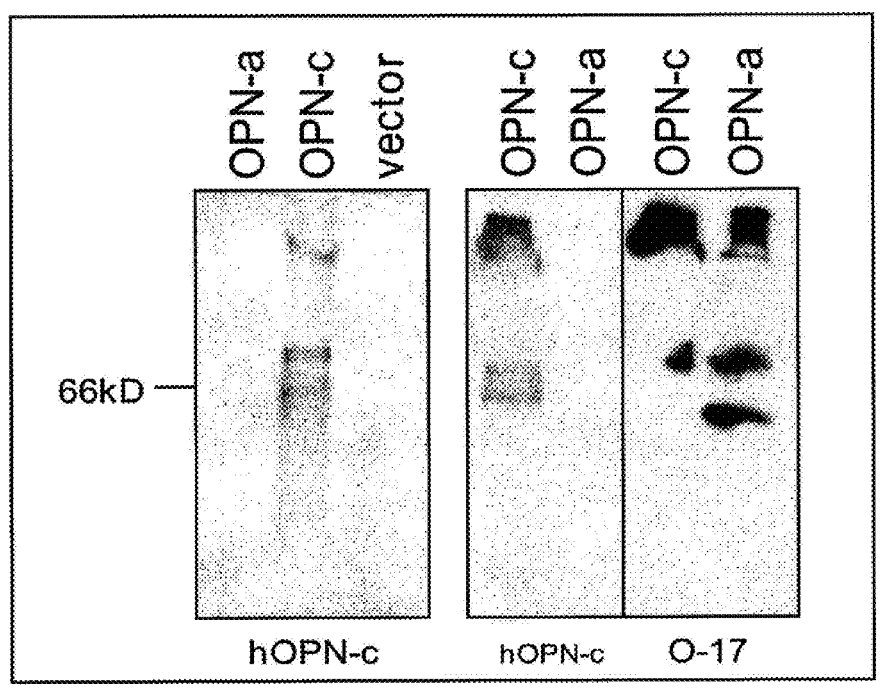
FIGS. 8A and 8B show the recognition of OPNc on Western blot or in histological sections by a specific antibody.
Figure 8B:
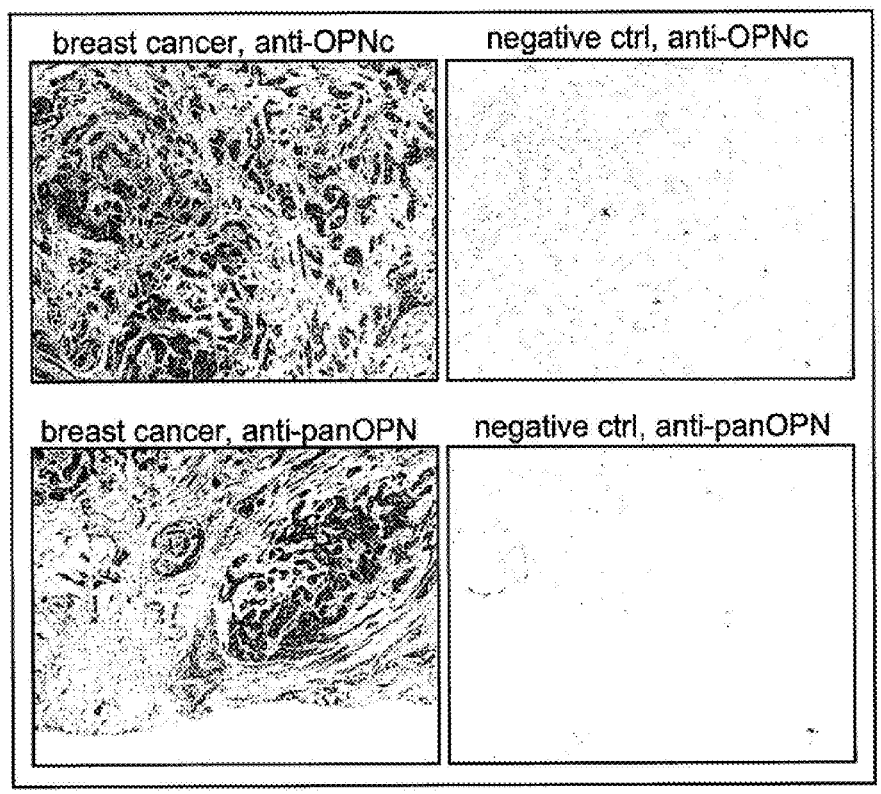

Specificity of the anti-hOPNc IgY antibody is shown in FIG. 8. Hens were immunized with a peptide representing the splice junction of human OPN-c. To mimic an internal sequence, the peptide was N-terminally acetylated. At the end of the immunization period, total immunoglobulin (IgY) was purified from eggs. FIG. 8A shows Western blotting with the left panel showing supernatants from transfected MCF-7 cells probed with the anti-hOPNc antibody (a prior Western blot of the same supernatants had demonstrated the comparable expression levels of OPN-a and -c). FIG. 8A right panel shows the loading of 400 ng of GST-OPN per lane, probed with anti-hOPNc, stripped, and reprobed with anti-pan-OPN 017. FIG. 8B shows staining of breast cancer tissue with an antibody to OPN-c (top left) or with an antibody to a common region of all splice variants (O-17, Assay Designs Inc.) (bottom left). The negative controls (top and bottom right) reflected the work-up without the primary antibody.

EXAMPLE 8

Synthetic peptide SEQ ID NO: 37 effects on soft agar clone formation by breast tumor cells. The peptide Ac-SGS-SEEKQNAVSSEET-NH$_2$ SEQ ID NO: 37, the sequence around the splice site in OPN-c SEQ ID NO: 2, was synthesized: (hOPN-c). The terminal acetylation and amidation made this peptide similar to an internal sequence (a sequence within a protein that is not at the N-terminal or C-terminal end).

To assess effect on soft agar colony formation, $5 \times 10^5$ MCF-7 cells per 60-mm dish were plated in triplicates with a top layer of 0.3% agar (BACTO Agar, Difco, Detroit Mich.) and a bottom layer of 0.5% agar (both in a-MEM). Peptide SEQ ID NO: 37 was added at the indicated concentrations upon plating and was replenished with every addition of medium. Every other day, 0.4 ml of medium was supplemented. After ten days, photographs were taken at high and low magnification and the surface area of all clones in five fields was measured with the imaging software ImageJ (NIH) or Metamorph.

The synthetic peptide SEQ ID NO: 37 mimicked the effect of OPN-c by increasing the size of the clones formed in soft agar after ten days. Two control peptides (hOPN-c scrambled sequence SEQ ID NO: 33 and hOPN-exon5 SEQ ID NO: 34) had no effect (data not shown). Similar results were obtained with MDA-MB-435 cells (not shown). For investigation of cell growth rates, MCF-7 cells were plated at 5000 cells/well in 24-well plates in the presence or absence of peptide. Daily, five wells per group were harvested by trypsinization and the cell numbers were determined in a Coulter™ Z-Series Counter. Consistent with previous results with OPN, SEQ ID NO: 37 had no effect on cell growth, which suggested its promotion of soft agar clone formation was based on its support of anchorage-independence, rather than accelerated cell cycle progression.

Figure 9A:
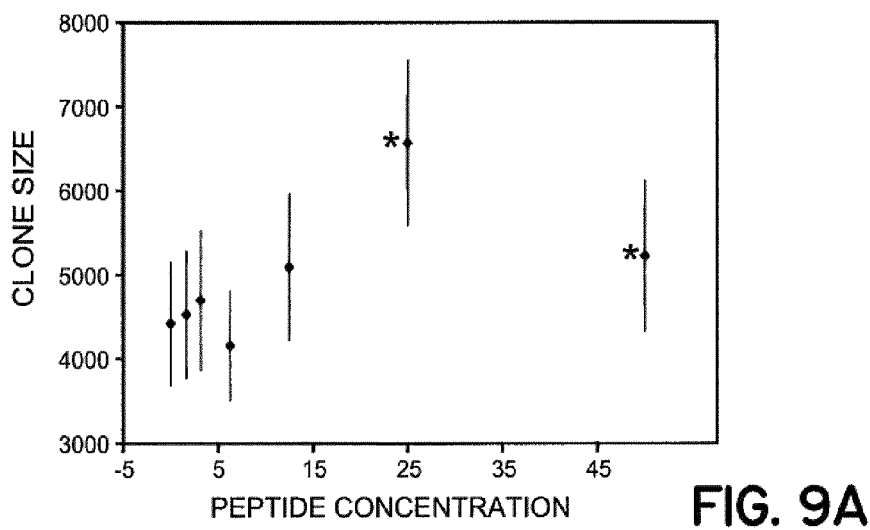
FIGS. 9A, 9B, and 9C show the effects of osteopontin-c peptide (OPNcPEP) on soft agar clone formation and on cell proliferation.
Figure 9B:
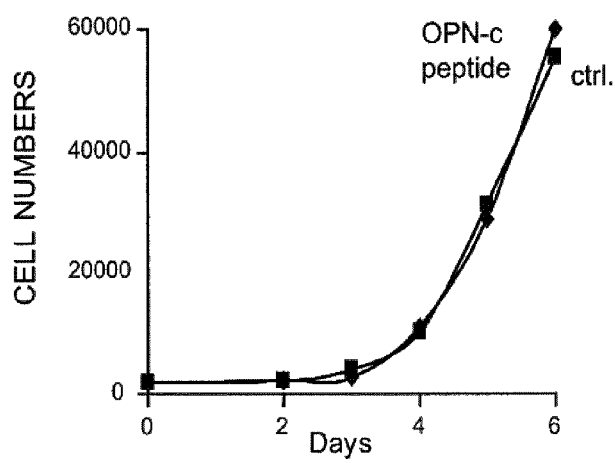
Figure 9C:
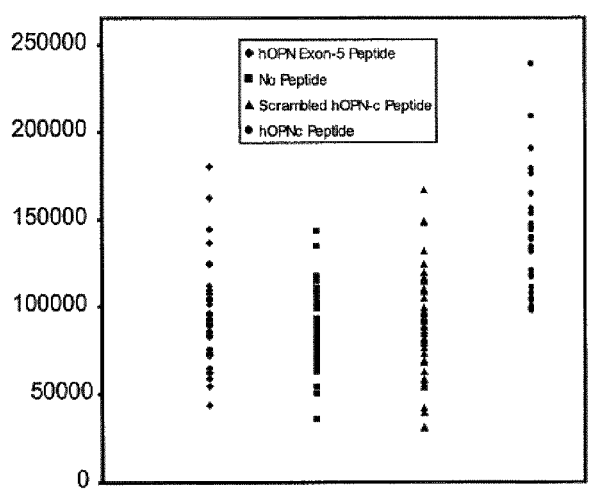

Results are shown in FIG. 9. $5 \times 10^5$ MCF-7 cells per 60-mm dish were plated in triplicates with a top layer of 0.3% agar (BACTO Agar, Difco, Detroit, Mich.) and a bottom layer of 0.5% agar (both in α-MEM). Peptide was added at the indicated concentrations upon plating and was replenished with every addition of medium. The size of the resultant colonies is shown in FIG. 9A. For the investigation of cell growth rates, MCF-7 cells were plated at 5000 cells/well in 24-well plates in the presence or absence of peptide. Daily, using five wells per group, cell numbers were determined and shown in FIG. 9B. Effects of a synthetic peptide on MDA-MB-435 cells are shown in FIG. 9C after 10 days in the presence or absence of synthetic peptides. hOPN Exon-5 peptide (NAVSSEETND-FKQE) SEQ ID NO: 34 and scrambled hOPN-c peptide (SSEEQETGVEKASSNS) SEQ ID NO: 33 served as non-specific controls.

EXAMPLE 9

Figure 10:
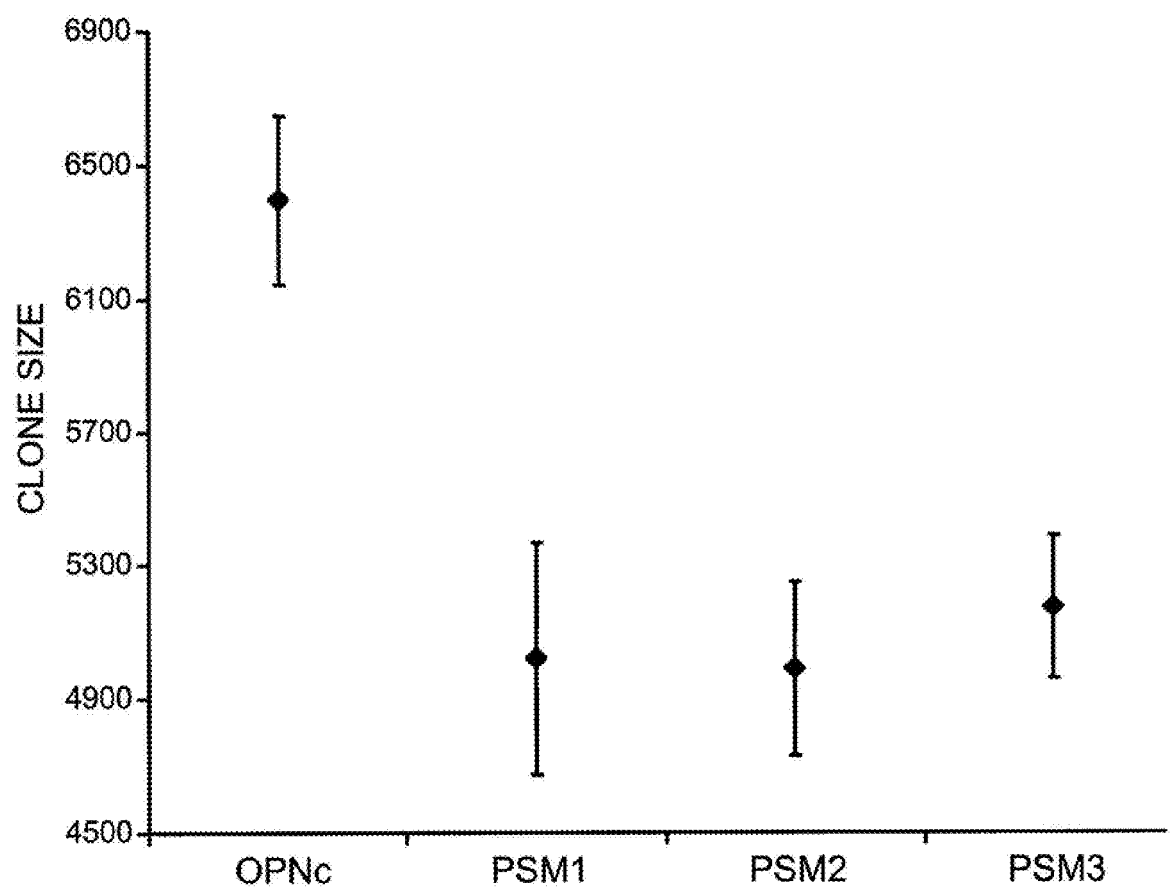
FIG. 10 shows the effect of modification of OPNcPEP on soft agar clone formation.

Role of phosphorylation in the biological function of OPNc. MCF-7 cells were stably transfected with expression constructs for OPNc SEQ ID NO: 7, PSM1 SEQ ID NO: 42, PSM2 SEQ ID NO: 43, or PSM3 SEQ ID NO: 44. PSM constructs are defined as targeted mutants of phosphorylation sites around the splice junction of OPNc SEQ ID NO: 7. The expressed protein OPNc SEQ ID NO: 7 contains the sequence SGSSEEKQNAVSSEET SEQ ID NO: 8 as a part of SEQ ID NO. 7. In PSM1, SEQ ID NO: 8 is mutated to SEQ ID NO: 42 AGAAEEKQNAVAAEEA. In PSM2, SEQ ID NO: 8 is mutated to SEQ ID NO: 43 AGAAEEKQNAVSSET. In PSM3, SEQ ID NO: 8 is mutated to SEQ ID NO: 44 SGS-SEEKQNAVAAEEA. To assess the effects of these constructs on soft agar colony formation, $5 \times 10^5$ MCF-7 cells stably transfected with OPNc SEQ ID NO: 7 or PSM1 SEQ ID NO: 42 or PSM2 SEQ ID NO: 43 or PSM3 SEQ ID NO: 44 were plated in triplicates with a top layer of 0.3% agar (BACTO Agar, Difco, Detroit Mich.) and a bottom layer of 0.5% agar (both in a-MEM). Every other day, 0.4 ml of medium was supplemented. After seven days, photographs were taken at high and low magnification and the surface area of all clones in five fields was measured with the imaging software ImageJ (NIH) or Metamorph. All targeted mutants were significantly less effective in supporting soft agar clone formation by MCF-7 cells than OPNc SEQ ID NO: 7 ($p<0.05$ t-test, error bars are SEM) as shown in FIG. 10.

It should be understood that the embodiments and examples described are only illustrative and are not limiting in any way. Therefore, various changes, modifications or alterations to these embodiments may be made or resorted to without departing from the spirit of the invention and the scope of the following claims.

What is claimed is:

1. A method to perturb physiologic cell survival, the method comprising
   providing an antagonist to SEQ ID NO: 8 to a cell under physiologic conditions, and
   thereafter assessing an activity indicating reduced survival of cells with a reduced substratum requirement after incubating the cells under physiologic conditions with the SEQ ID NO: 8 antagonist, wherein the SEQ ID NO: 8 antagonist is an antibody to at least one of
   SEQ ID NO: 35;
   SEQ ID NO: 8;
   a fragment of SEQ ID NO: 8 comprising SEQ ID NO: 35; or
   SEQ ID NO: 41.

2. The method of claim 1 wherein the activity is at least one of adhesion independence promotion or oxidoreductase expression stimulation.

3. The method of claim 1 wherein SEQ ID NO: 8, a fragment of SEQ ID NO: 8 comprising SEQ ID NO: 35, SEQ ID NO:41, or SEQ ID NO: 35 contains at least one of N-terminal acetylation, C-terminal amidation, an additional C-terminal cysteine, or a posttranslational modification.

4. The method of claim 3 wherein the posttranslational modification is phosphorylation.

5. A physiologic cell augmentation method comprising
providing to a cell under physiologic conditions an antagonist to SEQ ID NO: 8, and
thereafter assessing reduced expansion of cells with a reduced requirement for a substratum contact for cell survival, wherein the SEQ ID NO: 8 antagonist is an antibody to at least one of
SEQ ID NO: 35;
SEQ ID NO: 8;
a fragment of SEQ ID NO: 8 comprising SEQ ID NO: 35; or
SEQ ID NO: 41.

6. The method of claim 1 or claim 5 wherein cells with a reduced substratum requirement are malignant cells.

7. The method of claim 5 wherein SEQ ID NO: 8, a fragment of SEQ ID NO: 8 comprising SEQ ID NO: 35, SEQ ID NO:41, or SEQ ID NO: 35 contains at least one of N-terminal acetylation, C-terminal amidation, an additional C-terminal cysteine, or a posttranslational modification.

8. The method of claim 7 wherein the posttranslational modification is phosphorylation.

\* \* \* \* \*

SEQUENCE LISTING

<160> NUMBER OF SEQ ID NOS: 44

<210> SEQ ID NO 1
<211> LENGTH: 1641
<212> TYPE: DNA
<213> ORGANISM: human

<400> SEQUENCE: 1

```
ctccctgtgt tggtggagga tgtctgcagc agcatttaaa ttctgggagg gcttggttgt    60
cagcagcagc aggaggaggc agagcacagc atcgtcggga ccagactcgt tcaggccag   120
ttgcagcctt ctcagccaaa cgccgaccaa ggaaaactca ctaccatgag aattgcagtg   180
atttgctttt gcctcctagg catcacctgt gccataccag ttaaacaggc tgattctgga   240
agttctgagg aaaagcagct ttacaacaaa tacccagatg ctgtggccac atggctaaac   300
cctgacccat ctcagaagca gaatctccta gccccacaga tgctgtgtc ctctgaagaa   360
accaatgact ttaaacaaga gacccttcca gtaagtcca cgaaagcca tgaccacatg     420
gatgatatgg atgatgaaga tgatgatgac catgtggaca gccaggactc cattgactcg   480
aacgactctg atgatgtaga tgacactgat gattctcacc agtctgatga gtctcaccat   540
tctgatgaat ctgatgaact ggtcactgat tttcccacgg acctgccagc aaccgaagtt   600
ttcactccag ttgtccccac agtagacaca tatgatggcc gaggtgatag tgtggtttat   660
ggactgaggt caaaatctaa gaagtttcgc agacctgaca tccagtaccc tgatgctaca   720
gacgaggaca tcacctcaca catggaaagc gaggagttga tggtgcata caaggccatc   780
cccgttgccc aggacctgaa cgcgccttct gattgggaca gccgtgggaa ggacagttat   840
gaaacgagtc agctggatga ccagagtgct gaaacccaca gccacaagca gtccagatta   900
tataagcgga aagccaatga tgagagcaat gagcattccg atgtgattga tagtcaggaa   960
cttttccaaag tcagccgtga attccacagc catgaatttc acagccatga agatatgctg  1020
gttgtagacc ccaaaagtaa ggaagaagat aaacacctga aatttcgtat ttctcatgaa  1080
ttagatagtg catcttctga ggtcaattaa aaggagaaaa aatacaattt ctcactttgc  1140
atttagtcaa aagaaaaaat gctttatagc aaaatgaaag agaacatgaa atgcttcttt  1200
ctcagtttat tggttgaatg tgtatctatt tgagtctgga ataactaat gtgtttgata   1260
attagtttag tttgtggctt catggaaact ccctgtaaac taaagcttc agggttatgt   1320
ctatgttcat tctatagaag aaatgcaaac tatcactgta ttttaatatt tgttattctc  1380
tcatgaatag aaatttatgt agaagcaaac aaaatacttt tacccactta aaaagagaat  1440
ataacatttt atgtcactat aatcttttgt tttttaagtt agtgtatatt ttgttgtgat   1500
tatcttttg tggtgtgaat aaatcttta tcttgaatgt aataagaatt tggtggtgtc    1560
aattgcttat ttgttttccc acggttgtcc agcaattaat aaaacataac ctttttact   1620
gcctaaaaaa aaaaaaaaaa a                                             1641

<210> SEQ ID NO 2
<211> LENGTH: 945
<212> TYPE: DNA
<213> ORGANISM: human

<400> SEQUENCE: 2
atgagaattg cagtgatttg cttttgcctc ctaggcatca cctgtgccat accagttaaa    60
caggctgatt ctggaagttc tgaggaaaag cagctttaca caaataccc agatgctgtg   120
gccacatggc taaaccctga cccatctcag aagcagaatc tcctagcccc acagaatgct  180
gtgtcctctg aagaaccaa tgactttaaa caagagaccc ttccaagtaa gtccaacgaa   240
agccatgacc acatggatga tatggatgat gaagatgatg atgaccatgt ggacagccag   300
gactccattg actcgaacga ctctgatgat gtagatgaca ctgatgattc tcaccagtct   360
gatgagtctc accattctga tgaatctgat gaactggtca ctgattttcc cacggacctg   420
```

-continued

```
ccagcaaccg aagttttcac tccagttgtc cccacagtag acacatatga tggccgaggt    480
gatagtgtgg tttatggact gaggtcaaaa tctaagaagt ttcgcagacc tgacatccag    540
taccctgatg ctacagacga ggacatcacc tcacacatgg aaagcgagga gttgaatggt    600
gcatacaagg ccatcccgt tgcccaggac ctgaacgcgc cttctgattg gacagccgt     660 gggaaggaca gttatgaaac gagtcagctg gatgaccaga gtgctgaaac ccacagccac    720
aagcagtcca gattatataa gcggaaagcc aatgatgaga gcaatgagca ttccgatgtg    780
attgatagtc aggaactttc caaagtcagc cgtgaattcc acagccatga atttcacagc    840
catgaagata tgctggttgt agaccccaaa agtaaggaag aagataaaca cctgaaattt    900
cgtatttctc atgaattaga tagtgcatct tctgaggtca attaa                    945

<210> SEQ ID NO 3
<211> LENGTH: 1616
<212> TYPE: DNA
<213> ORGANISM: human

<400> SEQUENCE: 3
ctccctgtgt tggtggagga tgtctgcagc agcatttaaa ttctgggagg gcttggttgt     60
cagcagcagc aggaggaggc agagcacagc atcgtcggga ccagactcgt ctcaggccag    120
ttgcagcctt ctcagccaaa cgccgaccaa ggaaaactca ctaccatgag aattgcagtg    180
atttgctttt gcctcctagg catcacctgt gccataccag ttaaacaggc tgattctgga    240
agttctgagg aaaagcagct ttacaacaaa tacccagatg ctgtggccac atggctaaac    300
cctgacccat ctcagaagca gaatctccta gccccacaga cccttccaag taagtccaac    360
gaaagccatg accacatgga tgatatggat gatgaagatg atgatgacca tgtggacagc    420
caggactcca ttgactcgaa cgactctgat gatgtagatg acactgatga ttctcaccag    480
tctgatgagt ctcaccattc tgatgaatct gatgaactgg tcactgattt tcccacggac    540
ctgccagcaa ccgaagtttt cactccagtt gtccccacag tagacacata tgatggccga    600
ggtgatagtg tggtttatgg actgaggtca aaatctaaga gtttcgcag acctgacatc     660 cagtaccctg atgctacaga cgaggacatc acctcacaca tggaaagcga ggagttgaat    720
ggtgcataca aggccatccc cgttgcccag gacctgaacg cgccttctga ttgggacagc    780
cgtgggaagg acagttatga aacgagtcag ctggatgacc agagtgctga aacccacagc    840
cacaagcagt ccagattata taagcggaaa gccaatgatg agagcaatga gcattccgat    900
gtgattgata tcaggaact tccaaagtc agccgtgaat tccacagcca tgaatttcac    960
agccatgaag atatgctggt tgtagacccc aaaagtaagg aagaagataa acacctgaaa   1020
tttcgtattt ctcatgaatt agatagtgca tcttctgagg tcaattaaaa ggagaaaaaa   1080
tacaatttct cactttgcat ttagtcaaaa gaaaaaatgc tttatagcaa aatgaaagag   1140
aacatgaaat gcttctttct cagtttattg gttaatgtg tatctatttg agtctggaaa    1200
taactaatgt gtttgataat tagtttagtt tgtggcttca tggaaactcc ctgtaaacta   1260
aaagcttcag ggttatgtct atgttcattc tatagaagaa atgcaaacta tcactgtatt   1320
ttaatatttg ttattctctc atgaatagaa atttatgtag aagcaaacaa aatacttta    1380 cccacttaaa aagagaatat aacatttat gtcactataa tcttttgttt tttaagttag    1440
tgtatatttt gttgtgatta tcttttgtg gtgtgaataa atcttttatc ttgaatgtaa    1500
taagaatttg gtggtgtcaa ttgcttattt gttttcccac ggttgtccag caattaataa    1560 aacataaccct tttttactgc ctaaaaaaaa aaaaaaaaa aaaaaaaaaa aaaaaa      1616
```

<210> SEQ ID NO 4
<211> LENGTH: 903
<212> TYPE: DNA
<213> ORGANISM: human

<400> SEQUENCE: 4

```
atgagaattg cagtgatttg cttttgcctc ctaggcatca cctgtgccat accagttaaa      60
caggctgatt ctggaagttc tgaggaaaag cagctttaca caaataccc agatgctgtg     120
gccacatggc taaaccctga cccatctcag aagcagaatc tcctagcccc acagacccctt    180
ccaagtaagt ccaacgaaag ccatgaccac atggatgata tggatgatga agatgatgat    240
gaccatgtgg acagccagga ctccattgac tcgaacgact ctgatgatgt agatgacact    300
gatgattctc accagtctga tgagtctcac cattctgatg aatctgatga actggtcact    360
gattttccca cggacctgcc agcaaccgaa gttttcactc cagttgtccc cacagtagac    420
acatatgatg ccgaggtga tagtgtggtt tatggactga ggtcaaaatc taagaagttt    480
cgcagacctg acatccagta ccctgatgct acagacgagg acatcaccctc acacatggaa    540
agcgaggagt tgaatggtgc atacaaggcc atccccgttg cccaggacct gaacgcgcct    600
tctgattggg acagccgtgg gaaggacagt tatgaaacga gtcagctgga tgaccagagt    660
gctgaaaccc cagccacaa gcagtccaga ttatataagc ggaaagccaa tgatgagagc    720
aatgagcatt ccgatgtgat tgatagtcag gaactttcca agtcagccg tgaattccac    780
agccatgaat tcacagcca tgaagatatg ctggttgtag acccaaaag taaggaagaa    840
gataaacacc tgaaatttcg tatttctcat gaattagata gtgcatcttc tgaggtcaat    900
taa                                                                   903
```

<210> SEQ ID NO 5
<211> LENGTH: 1560
<212> TYPE: DNA
<213> ORGANISM: human

<400> SEQUENCE: 5

```
ctccctgtgt tggtggagga tgtctgcagc agcatttaaa ttctgggagg gcttggttgt      60
cagcagcagc aggaggaggc agagcacagc atcgtcggga ccagactcgt ctcaggccag    120
ttgcagcctt ctcagccaaa cgccgaccaa ggaaaactca ctaccatgag aattgcagtg    180
atttgctttt gcctcctagg catcacctgt gccataccag ttaaacaggc tgattctgga    240
agttctgagg aaaagcagaa tgctgtgtcc tctgaagaaa ccaatgactt taaacaagag    300
acccttccaa gtaagtccaa cgaaagccat gaccacatgg atgatatgga tgatgaagat    360
gatgatgacc atgtggacag ccaggactcc attgactcga acgactctga tgatgtagat    420
gacactgatg attctcacca gtctgatgag tctcaccatt ctgatgaatc tgatgaactg    480
gtcactgatt ttcccacgga cctgccagca accgaagttt tcactccagt tgtccccaca    540
gtagacacat atgatggccg aggtgatagt gtggtttatg gactgaggtc aaaatctaag    600
aagtttcgca gacctgacat ccagtacct gatgctacag acgaggacat cacctcacac    660
atggaaagcg aggagttgaa tggtgcatac aaggccatcc ccgttgccca ggacctgaac    720
gcgccttctg attgggacag ccgtgggaag gacagttatg aaacgagtca gctggatgac    780
cagagtgctg aaacccacag ccacaagcag tccagattat ataagcggaa agccaatgat    840
gagagcaatg agcattccga tgtgattgat agtcaggaac tttccaaagt cagccgtgaa    900
```

| | |
|---|---|
| ttccacagcc atgaatttca cagccatgaa gatatgctgg ttgtagaccc caaaagtaag | 960 |
| gaagaagata aacacctgaa atttcgtatt tctcatgaat tagatagtgc atcttctgag | 1020 |
| gtcaattaaa aggagaaaaa atacaatttc tcactttgca tttagtcaaa agaaaaaatg | 1080 |
| ctttatagca aaatgaaaga gaacatgaaa tgcttctttc tcagtttatt ggttgaatgt | 1140 |
| gtatctattt gagtctggaa ataactaatg tgtttgataa ttagtttagt ttgtggcttc | 1200 |
| atggaaactc cctgtaaact aaaagcttca gggttatgtc tatgttcatt ctatagaaga | 1260 |
| aatgcaaact atcactgtat tttaatattt gttattctct catgaataga aatttatgta | 1320 |
| gaagcaaaca aaatactttt acccacttaa aaagagaata taacatttta tgtcactata | 1380 |
| atcttttgtt ttttaagtta gtgtatattt tgttgtgatt atcttttttgt ggtgtgaata | 1440 |
| aatcttttat cttgaatgta ataagaattt ggtggtgtca attgcttatt tgttttccca | 1500 |
| cggttgtcca gcaattaata aaacataacc tttttttactg cctaaaaaaa aaaaaaaaaa | 1560 |

<210> SEQ ID NO 6
<211> LENGTH: 864
<212> TYPE: DNA
<213> ORGANISM: human

<400> SEQUENCE: 6

| | |
|---|---|
| atgagaattg cagtgatttg cttttgcctc ctaggcatca cctgtgccat accagttaaa | 60 |
| caggctgatt ctggaagttc tgaggaaaag cagaatgctg tgtcctctga agaaaccaat | 120 |
| gactttaaac aagagaccct tccaagtaag tccaacgaaa gccatgacca catggatgat | 180 |
| atggatgatg aagatgatga tgaccatgtg gacagccagg actccattga ctcgaacgac | 240 |
| tctgatgatg tagatgacac tgatgattct caccagtctg atgagtctca ccattctgat | 300 |
| gaatctgatg aactggtcac tgattttccc acggacctgc cagcaaccga agttttcact | 360 |
| ccagttgtcc ccacagtaga cacatatgat ggccgaggtg atagtgtggt ttatggactg | 420 |
| aggtcaaaat ctaagaagtt tcgcagacct gacatccagt accctgatgc tacagacgag | 480 |
| gacatcacct cacacatgga aagcgaggag ttgaatggtg catacaaggc catccccgtt | 540 |
| gcccaggacc tgaacgcgcc ttctgattgg gacagccgtg gaaggacag ttatgaaacg | 600 |
| agtcagctgg atgaccagag tgctgaaacc cacagccaca gcagtccag attatataag | 660 |
| cggaaagcca atgatgagag caatgagcat tccgatgtga ttgatagtca ggaactttcc | 720 |
| aaagtcagcc gtgaattcca cagccatgaa tttcacagcc atgaagatat gctggttgta | 780 |
| gaccccaaaa gtaaggaaga agataaacac ctgaaatttc gtatttctca tgaattagat | 840 |
| agtgcatctt ctgaggtcaa ttaa | 864 |

<210> SEQ ID NO 7
<211> LENGTH: 287
<212> TYPE: PRT
<213> ORGANISM: human

<400> SEQUENCE: 7

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Asn
            20                  25                  30

Ala Val Ser Ser Glu Glu Thr Asn Asp Phe Lys Gln Glu Thr Leu Pro
        35                  40                  45

Ser Lys Ser Asn Glu Ser His Asp His Met Asp Asp Met Asp Asp Glu
    50                  55                  60

```
Asp Asp Asp Asp His Val Ser Gln Asp Ser Ile Asp Ser Asn Asp
 65                  70                  75                  80

Ser Asp Asp Val Asp Thr Asp Ser His Gln Ser Asp Glu Ser
             85                  90                  95

His His Ser Asp Glu Ser Asp Glu Leu Val Thr Asp Phe Pro Thr Asp
            100                 105                 110

Leu Pro Ala Thr Glu Val Phe Thr Pro Val Val Pro Thr Val Asp Thr
            115                 120                 125

Tyr Asp Gly Arg Gly Asp Ser Val Val Tyr Gly Leu Arg Ser Lys Ser
130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
                165                 170                 175

Ala Ile Pro Val Ala Gln Asp Leu Asn Ala Pro Ser Asp Trp Asp Ser
            180                 185                 190

Arg Gly Lys Asp Ser Tyr Glu Thr Ser Gln Leu Asp Asp Gln Ser Ala
            195                 200                 205

Glu Thr His Ser His Lys Gln Ser Arg Leu Tyr Lys Arg Lys Ala Asn
210                 215                 220

Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
                245                 250                 255

Met Leu Val Val Asp Pro Lys Ser Lys Glu Glu Asp Lys His Leu Lys
            260                 265                 270

Phe Arg Ile Ser His Glu Leu Asp Ser Ala Ser Ser Glu Val Asn
            275                 280                 285

<210> SEQ ID NO 8
<211> LENGTH: 16
<212> TYPE: PRT
<213> ORGANISM: Artificial
<220> FEATURE:
<223> OTHER INFORMATION: Peptide representing a domain encompassing the
      splice junction of Exon 3 and 5

<400> SEQUENCE: 8

Ser Gly Ser Ser Glu Glu Lys Gln Asn Ala Val Ser Ser Glu Glu Thr
1               5                   10                  15

<210> SEQ ID NO 9
<211> LENGTH: 20
<212> TYPE: DNA
<213> ORGANISM: Artificial
<220> FEATURE:
<223> OTHER INFORMATION: 5' (forward) primer for RT-PCR of OPNa

<400> SEQUENCE: 9
atctcctagc cccacagaat                                              20

<210> SEQ ID NO 10
<211> LENGTH: 22
<212> TYPE: DNA
<213> ORGANISM: Artificial
<220> FEATURE:
<223> OTHER INFORMATION: 3' (reverse) RT-PCR primer for OPNa

<400> SEQUENCE: 10
```

```
catcagactg gtgagaatca tc                                              22

<210> SEQ ID NO 11
<211> LENGTH: 18
<212> TYPE: DNA
<213> ORGANISM: Artificial
<220> FEATURE:
<223> OTHER INFORMATION: 5' (forward) RT-PCR primer for OPNc

<400> SEQUENCE: 11
ctgaggaaaa gcagaatg                                                   18

<210> SEQ ID NO 12
<211> LENGTH: 17
<212> TYPE: DNA
<213> ORGANISM: Artificial
<220> FEATURE:
<223> OTHER INFORMATION: 3' (reverse) RT-PCR primer for OPNc

<400> SEQUENCE: 12
aatggagtcc tggctgt                                                    17

<210> SEQ ID NO 13
<211> LENGTH: 26
<212> TYPE: DNA
<213> ORGANISM: Artificial
<220> FEATURE:
<223> OTHER INFORMATION: 5' (forward) RT-PCR primer for GAPDH

<400> SEQUENCE: 13
tgaaggtcgg agtcaacgga tttggt                                          26

<210> SEQ ID NO 14
<211> LENGTH: 24
<212> TYPE: DNA
<213> ORGANISM: Artificial
<220> FEATURE:
<223> OTHER INFORMATION: 3' (reverse) RT-PCR primer for GADPH

<400> SEQUENCE: 14
catgtgggcc atgaggtcca ccac                                            24

<210> SEQ ID NO 15
<211> LENGTH: 22
<212> TYPE: DNA
<213> ORGANISM: Artificial
<220> FEATURE:
<223> OTHER INFORMATION: 5' (forward) CDS primer for OPN

<400> SEQUENCE: 15
caaacgccga ccaagggaaa ac                                              22

<210> SEQ ID NO 16
<211> LENGTH: 21
<212> TYPE: DNA
<213> ORGANISM: Artificial
<220> FEATURE:
<223> OTHER INFORMATION: 3' (reverse) CDS primer for OPN

<400> SEQUENCE: 16
cttctttctc agtttattgg t                                               21

<210> SEQ ID NO 17
<211> LENGTH: 31
<212> TYPE: DNA
<213> ORGANISM: Artificial
```

```
<220> FEATURE:
<223> OTHER INFORMATION: 5' (forward) primer for GST-OPN

<400> SEQUENCE: 17
cgggatcccc ataccagtta aacaggctga t                              31

<210> SEQ ID NO 18
<211> LENGTH: 29
<212> TYPE: DNA
<213> ORGANISM: Artificial
<220> FEATURE:
<223> OTHER INFORMATION: 3' (reverse) primer for GST-OPN

<400> SEQUENCE: 18
ggctcgagat gttctctttc attttgcta                                 29

<210> SEQ ID NO 19
<211> LENGTH: 22
<212> TYPE: DNA
<213> ORGANISM: Artificial
<220> FEATURE:
<223> OTHER INFORMATION: 5' (forward) PCR primer for OPN region 50 - 246

<400> SEQUENCE: 19
taccagttaa acaggctgat tc                                        22

<210> SEQ ID NO 20
<211> LENGTH: 20
<212> TYPE: DNA
<213> ORGANISM: Artificial
<220> FEATURE:
<223> OTHER INFORMATION: 3' (reverse) PCR primer for OPN region 50 - 246

<400> SEQUENCE: 20
ccatatcatc catgtggtca                                           20

<210> SEQ ID NO 21
<211> LENGTH: 19
<212> TYPE: DNA
<213> ORGANISM: Artificial
<220> FEATURE:
<223> OTHER INFORMATION: 5' (forward) primer for OPNb

<400> SEQUENCE: 21
atctcctagc cccagagac                                            19

<210> SEQ ID NO 22
<211> LENGTH: 23
<212> TYPE: DNA
<213> ORGANISM: Artificial
<220> FEATURE:
<223> OTHER INFORMATION: 3' (reverse) primer for OPNb

<400> SEQUENCE: 22
aaaatcagtg accagttcat cag                                       23

<210> SEQ ID NO 23
<211> LENGTH: 20
<212> TYPE: DNA
<213> ORGANISM: Artificial
<220> FEATURE:
<223> OTHER INFORMATION: 5' (forward) primer for OPNc

<400> SEQUENCE: 23
tgaggaaaag cagaatgctg                                           20
```

```
<210> SEQ ID NO 24
<211> LENGTH: 20
<212> TYPE: DNA
<213> ORGANISM: Artificial
<220> FEATURE:
<223> OTHER INFORMATION: 3' (reverse) primer for OPNc

<400> SEQUENCE: 24
gtcaatggag tcctggctgt                                               20

<210> SEQ ID NO 25
<211> LENGTH: 21
<212> TYPE: DNA
<213> ORGANISM: Artificial
<220> FEATURE:
<223> OTHER INFORMATION: 5' (forward) primer for beta actin

<400> SEQUENCE: 25
ggcggcacca ccatgtaccc t                                             21

<210> SEQ ID NO 26
<211> LENGTH: 21
<212> TYPE: DNA
<213> ORGANISM: Artificial
<220> FEATURE:
<223> OTHER INFORMATION: 3' (reverse) primer for beta actin

<400> SEQUENCE: 26
aggggccgga ctcgtcatac t                                             21

<210> SEQ ID NO 27
<211> LENGTH: 19
<212> TYPE: DNA
<213> ORGANISM: Artificial
<220> FEATURE:
<223> OTHER INFORMATION: 5' (forward) primer for Ck-19

<400> SEQUENCE: 27
cccgcgacta cagccacta                                                19

<210> SEQ ID NO 28
<211> LENGTH: 19
<212> TYPE: DNA
<213> ORGANISM: Artificial
<220> FEATURE:
<223> OTHER INFORMATION: 3' (reverse) primer for Ck-19

<400> SEQUENCE: 28
ctcatgcgca gagcctgtt                                                19

<210> SEQ ID NO 29
<211> LENGTH: 20
<212> TYPE: DNA
<213> ORGANISM: Artificial
<220> FEATURE:
<223> OTHER INFORMATION: 5' (forward) primer for aP2

<400> SEQUENCE: 29
tcagtgtgaa tggggatgtg                                               20

<210> SEQ ID NO 30
<211> LENGTH: 20
<212> TYPE: DNA
<213> ORGANISM: Artificial
<220> FEATURE:
<223> OTHER INFORMATION: 3' (reverse) primer for aP2
```

<400> SEQUENCE: 30
gtggaagtga cgcctttcat                                               20

<210> SEQ ID NO 31
<211> LENGTH: 5
<212> TYPE: PRT
<213> ORGANISM: Artificial
<220> FEATURE:
<223> OTHER INFORMATION: alphavbeta3 integrin binding peptide

<400> SEQUENCE: 31

Gly Arg Gly Asp Ser
1               5

<210> SEQ ID NO 32
<211> LENGTH: 7
<212> TYPE: PRT
<213> ORGANISM: Artificial
<220> FEATURE:
<223> OTHER INFORMATION: beta1-containg integrin binding peptide

<400> SEQUENCE: 32

Ser Val Val Tyr Gly Leu Arg
1               5

<210> SEQ ID NO 33
<211> LENGTH: 16
<212> TYPE: PRT
<213> ORGANISM: artificial
<220> FEATURE:
<223> OTHER INFORMATION: Control peptide for OPNcPEP

<400> SEQUENCE: 33

Ser Ser Glu Glu Gln Glu Thr Gly Val Glu Lys Ala Ser Ser Asn Ser
1               5                   10                  15

<210> SEQ ID NO 34
<211> LENGTH: 14
<212> TYPE: PRT
<213> ORGANISM: Artificial
<220> FEATURE:
<223> OTHER INFORMATION: Control peptide derived from Exon 5

<400> SEQUENCE: 34

Asn Ala Val Ser Ser Glu Glu Thr Asn Asp Phe Lys Gln Glu
1               5                   10

<210> SEQ ID NO 35
<211> LENGTH: 7
<212> TYPE: PRT
<213> ORGANISM: Artificial
<220> FEATURE:
<223> OTHER INFORMATION: OPNcPEP inhibitor peptide

<400> SEQUENCE: 35

Glu Glu Lys Gln Asn Ala Val
1               5

<210> SEQ ID NO 36
<211> LENGTH: 48
<212> TYPE: DNA
<213> ORGANISM: Artificial
<220> FEATURE:
<223> OTHER INFORMATION: DNA sequence coding for OPNcPEP

<400> SEQUENCE: 36

```
tctggaagtt ctgaggaaaa gcagaatgct gtgtcctctg aagaaacc                48
```

<210> SEQ ID NO 37
<211> LENGTH: 16
<212> TYPE: PRT
<213> ORGANISM: Artificial
<220> FEATURE:
<223> OTHER INFORMATION: Modified OPNcPEP
<220> FEATURE:
<221> NAME/KEY: MISC_FEATURE
<222> LOCATION: (1)..()
<223> OTHER INFORMATION: N-Terminal Acetylation
<220> FEATURE:
<221> NAME/KEY: MISC_FEATURE
<222> LOCATION: (16)..()
<223> OTHER INFORMATION: C-Terminal Amidation

<400> SEQUENCE: 37

```
Ser Gly Ser Ser Glu Glu Lys Gln Asn Ala Val Ser Ser Glu Glu Thr
1               5                   10                  15
```

<210> SEQ ID NO 38
<211> LENGTH: 11
<212> TYPE: PRT
<213> ORGANISM: Artificial
<220> FEATURE:
<223> OTHER INFORMATION: Truncation of OPNcPEP to 12AA

<400> SEQUENCE: 38

```
Ser Ser Glu Glu Lys Gln Asn Ala Val Ser Ser
1               5                   10
```

<210> SEQ ID NO 39
<211> LENGTH: 5
<212> TYPE: PRT
<213> ORGANISM: Artificial
<220> FEATURE:
<223> OTHER INFORMATION: Truncated OPNcPEP of 5AA

<400> SEQUENCE: 39

```
Glu Lys Gln Asn Ala
1               5
```

<210> SEQ ID NO 40
<211> LENGTH: 813
<212> TYPE: DNA
<213> ORGANISM: Artificial
<220> FEATURE:
<223> OTHER INFORMATION: OPNcPEP nucleotide conjugated with GST
      encoding sequence

<400> SEQUENCE: 40

```
ataccagtta aacaggctga ttctggaagt tctgaggaaa agcagaatgc tgtgtcctct     60
gaagaaacca atgactttaa acaagagacc cttccaagta agtccaacga aagccatgac    120
cacatggatg atatggatga tgaagatgat gatgaccatg tggacagcca ggactccatt    180
gactcgaacg actctgatga tgtagatgac actgatgatt ctcaccagtc tgatgagtct    240
caccattctg atgaatctga tgaactggtc actgattttc ccacggacct gccagcaacc    300
gaagttttca ctccagttgt ccccacagta gacacatata tggccgaggt gatagtgtg    360
gtttatggac tgaggtcaaa atctaagaag tttcgcagac ctgacatcca gtaccctgat    420
gctacagacg agcacatcac ctcacacatg gaaagcgagg agttgaatgg tgcatacaag    480
gccatccccg ttgcccagga cctgaacgcg ccttctgatt gggacagccg tgggaaggac    540
```

```
agttatgaaa cgagtcagct ggatgaccag agtgctgaag cccacagcca caagcagtcc      600
agattatata agcggaaagc taatgatgag agcaatgagc attccgatgt gattgatagt      660
caggaacttt ccaaagtcag ccgtgaattc cacagccatg aatttcacag ccatgaagat      720
atgctggttg tagaccccaa aagtaaggaa gaagataaac acctgaaatt tcgtatttct      780
catgaattag atagtgcatc ttctgaggtc aat                                    813
```

```
<210> SEQ ID NO 41
<211> LENGTH: 10
<212> TYPE: PRT
<213> ORGANISM: Artificial
<220> FEATURE:
<223> OTHER INFORMATION: OPNcPEP truncation with N-terminal acetylation
      and addition of C-terminal cysteine

<400> SEQUENCE: 41

Ser Glu Glu Lys Gln Asn Ala Val Ser Cys
1               5                   10

<210> SEQ ID NO 42
<211> LENGTH: 16
<212> TYPE: PRT
<213> ORGANISM: Artificial
<220> FEATURE:
<223> OTHER INFORMATION: Phosphorylation site mutant 1 of OPNcPEP

<400> SEQUENCE: 42

Ala Gly Ala Ala Glu Glu Lys Gln Asn Ala Val Ala Ala Glu Glu Ala
1               5                   10                  15

<210> SEQ ID NO 43
<211> LENGTH: 15
<212> TYPE: PRT
<213> ORGANISM: Artificial
<220> FEATURE:
<223> OTHER INFORMATION: phosphorylation site mutant 2 of OPNcPEP

<400> SEQUENCE: 43

Ala Gly Ala Ala Glu Glu Lys Gln Asn Ala Val Ser Ser Glu Thr
1               5                   10                  15

<210> SEQ ID NO 44
<211> LENGTH: 16
<212> TYPE: PRT
<213> ORGANISM: Artificial
<220> FEATURE:
<223> OTHER INFORMATION: phosphorylation site mutant 3 of OPNcPEP

<400> SEQUENCE: 44

Ser Gly Ser Ser Glu Glu Lys Gln Asn Ala Val Ala Ala Glu Glu Ala
1               5                   10                  15
```